US011813410B2

(12) United States Patent
Olson et al.

(10) Patent No.: US 11,813,410 B2
(45) Date of Patent: Nov. 14, 2023

(54) CONTROLLABLE EXPANDABLE CATHETER

(71) Applicant: St. Jude Medical, Cardiology Division, Inc., St. Paul, MN (US)

(72) Inventors: Gregory K. Olson, Elk River, MN (US); Rishi Manda, Stillwater, MN (US); Travis Dahlen, Forest Lake, MN (US); Troy T. Tegg, Elk River, MN (US); Brian M. Monahan, Elk River, MN (US); Russell D Terwey, St. Michael, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 453 days.

(21) Appl. No.: 16/767,081

(22) PCT Filed: Nov. 28, 2018

(86) PCT No.: PCT/US2018/062865
§ 371 (c)(1),
(2) Date: May 26, 2020

(87) PCT Pub. No.: WO2019/108664
PCT Pub. Date: Jun. 6, 2019

(65) Prior Publication Data
US 2020/0375657 A1 Dec. 3, 2020

Related U.S. Application Data

(60) Provisional application No. 62/591,278, filed on Nov. 28, 2017, provisional application No. 62/743,389, filed on Oct. 9, 2018.

(51) Int. Cl.
*A61M 25/01* (2006.01)
*A61B 17/34* (2006.01)
(Continued)

(52) U.S. Cl.
CPC .... *A61M 25/0026* (2013.01); *A61M 25/0009* (2013.01); *A61M 25/0032* (2013.01);
(Continued)

(58) Field of Classification Search
None
See application file for complete search history.

(56) References Cited

U.S. PATENT DOCUMENTS 5,224,939 A 7/1993 Holman et al.
5,380,301 A 1/1995 Prichard et al.
(Continued)

FOREIGN PATENT DOCUMENTS

CN 201275144 Y 7/2009
CN 101686848 A 3/2010
(Continued)

*Primary Examiner* — Ann Schillinger
(74) *Attorney, Agent, or Firm* — Kilpatrick Townsend & Stockton LLP

(57) ABSTRACT

An elongate medical device comprising an expandable structure with an expandable configuration and a collapsed configuration, a handle, operably coupled to the expandable structure, the handle further including a selective movement limiter; and a deflection control member coupled with the distal hub, where the deflection control member is configured to adjust a stiffness of the expandable structure, from a first stiffness to a second stiffness, and maintain the first stiffness or the second stiffness when the selective movement limiter couples with the deflection control member and limits a longitudinal movement of the deflection control member, and wherein the deflection control member is configured to move freely when the selective movement limiter is not coupled with the deflection control member.

22 Claims, 11 Drawing Sheets

(51) Int. Cl.
    *A61B 17/00*     (2006.01)
    *A61B 5/02*     (2006.01)
    *A61M 25/00*     (2006.01)
    *A61M 25/10*     (2013.01)
    *A61B 18/14*     (2006.01)
    *A61B 18/02*     (2006.01)
    *A61B 18/00*     (2006.01)
    *A61B 34/00*     (2016.01)

(52) U.S. Cl.
    CPC ........ *A61M 25/0144* (2013.01); *A61M 25/10* (2013.01); *A61B 18/1492* (2013.01); *A61B 34/25* (2016.02); *A61B 2017/00327* (2013.01); *A61B 2017/00867* (2013.01); *A61B 2018/00357* (2013.01); *A61B 2018/00577* (2013.01); *A61B 2018/00791* (2013.01); *A61B 2018/00821* (2013.01); *A61B 2018/0212* (2013.01); *A61B 2018/1405* (2013.01); *A61B 2218/002* (2013.01); *A61M 25/0045* (2013.01); *A61M 25/0054* (2013.01); *A61M 25/0136* (2013.01); *A61M 25/0141* (2013.01); *A61M 25/0147* (2013.01); *A61M 2025/0035* (2013.01); *A61M 2025/0036* (2013.01); *A61M 2025/0037* (2013.01); *A61M 2025/0046* (2013.01); *A61M 2025/0063* (2013.01)

(56) References Cited

U.S. PATENT DOCUMENTS

| | | | |
|---|---|---|---|
| 5,400,783 A * | 3/1995 | Pomeranz | A61N 1/06 600/374 |
| 5,456,254 A | 10/1995 | Pietroski et al. | |
| 5,626,136 A | 5/1997 | Webster, Jr. | |
| 5,715,817 A | 2/1998 | Stevens-Wright et al. | |
| 5,715,832 A | 2/1998 | Koblish et al. | |
| 5,722,401 A * | 3/1998 | Pietroski | A61B 5/6858 600/374 |
| 5,782,239 A * | 7/1998 | Webster, Jr. | A61B 5/6858 600/374 |
| 5,827,278 A | 10/1998 | Webster, Jr. | |
| 5,871,483 A * | 2/1999 | Jackson | A61B 18/1492 606/41 |
| 5,876,373 A | 3/1999 | Giba et al. | |
| 6,014,579 A * | 1/2000 | Pomeranz | A61B 5/6858 606/41 |
| 6,074,379 A | 6/2000 | Prichard | |
| 6,273,404 B1 | 8/2001 | Holman et al. | |
| 6,491,681 B1 | 12/2002 | Kunis et al. | |
| 6,554,794 B1 | 4/2003 | Mueller et al. | |
| 7,004,937 B2 | 2/2006 | Lentz et al. | |
| 7,214,220 B2 | 5/2007 | McGlinch et al. | |
| 7,217,256 B2 | 5/2007 | Di Palma | |
| 7,263,397 B2 | 8/2007 | Hauck et al. | |
| 7,386,339 B2 | 6/2008 | Strommer et al. | |
| 7,608,063 B2 | 10/2009 | Le et al. | |
| 7,625,365 B2 | 12/2009 | McGlinch et al. | |
| 7,666,204 B2 | 2/2010 | Thornton et al. | |
| 7,959,601 B2 | 6/2011 | McDaniel et al. | |
| 7,985,215 B2 | 7/2011 | Guo et al. | |
| 8,103,327 B2 | 1/2012 | Harlev et al. | |
| 8,137,321 B2 | 3/2012 | Argentine | |
| 8,221,390 B2 | 7/2012 | Pal et al. | |
| 8,273,016 B2 | 9/2012 | O'sullivan | |
| 8,376,990 B2 | 2/2013 | Ponzi et al. | |
| 8,447,377 B2 | 5/2013 | Harlev et al. | |
| 8,454,596 B2 | 6/2013 | Ma et al. | |
| 8,608,703 B2 | 12/2013 | Riles et al. | |
| 8,649,880 B1 | 2/2014 | Parker, Jr. | |
| 8,676,290 B2 | 3/2014 | Tegg | |
| 8,700,120 B2 | 4/2014 | Koblish | |
| 8,706,193 B2 | 4/2014 | Govari et al. | |
| 8,755,861 B2 | 6/2014 | Harlev et al. | |
| 8,777,929 B2 | 7/2014 | Schneider et al. | |
| 8,792,962 B2 | 7/2014 | Esguerra et al. | |
| 8,814,824 B2 | 8/2014 | Kauphusman et al. | |
| 8,814,825 B2 | 8/2014 | Tegg et al. | |
| 8,882,705 B2 | 11/2014 | McDaniel et al. | |
| 8,894,610 B2 | 11/2014 | Macnamara et al. | |
| 8,996,091 B2 | 3/2015 | de la Rama et al. | |
| 9,017,308 B2 | 4/2015 | Klisch et al. | |
| 9,033,917 B2 | 5/2015 | Magana et al. | |
| 9,050,010 B2 | 6/2015 | Bui et al. | |
| 9,101,733 B2 | 8/2015 | McDaniel | |
| 9,204,929 B2 * | 12/2015 | Solis | A61B 5/287 |
| 9,216,056 B2 | 12/2015 | Datta et al. | |
| 9,247,990 B2 | 2/2016 | Kauphusman et al. | |
| 9,326,815 B2 | 5/2016 | Watson | |
| 9,339,631 B2 | 5/2016 | Graham et al. | |
| 9,433,751 B2 | 9/2016 | Ponzi et al. | |
| 9,433,752 B2 | 9/2016 | Jimenez et al. | |
| 9,456,733 B2 * | 10/2016 | Smith | A61B 1/005 |
| 9,468,495 B2 | 10/2016 | Kunis et al. | |
| 9,486,280 B2 | 11/2016 | Koblish et al. | |
| 9,486,282 B2 | 11/2016 | Solis | |
| 9,539,413 B2 | 1/2017 | Ogle | |
| 9,649,158 B2 | 5/2017 | Datta et al. | |
| 9,687,166 B2 | 6/2017 | Subramaniam et al. | |
| 9,693,733 B2 | 7/2017 | Altmann et al. | |
| 9,693,820 B2 | 7/2017 | Koyrakh et al. | |
| 9,694,159 B2 | 7/2017 | Schneider et al. | |
| 9,694,161 B2 | 7/2017 | Selkee | |
| 9,788,895 B2 | 10/2017 | Solis | |
| 9,820,664 B2 | 11/2017 | Hoitink et al. | |
| 9,844,645 B2 | 12/2017 | Pai et al. | |
| 9,848,795 B2 | 12/2017 | Marecki et al. | |
| 9,919,132 B2 | 3/2018 | Tegg et al. | |
| 9,986,949 B2 | 6/2018 | Govari et al. | |
| 10,004,877 B2 | 6/2018 | Tegg | |
| 10,034,637 B2 | 7/2018 | Harlev et al. | |
| 10,052,457 B2 | 8/2018 | Nguyen et al. | |
| 10,065,019 B2 | 9/2018 | Hamuro et al. | |
| 10,099,036 B2 | 10/2018 | Heideman et al. | |
| 10,118,022 B2 | 11/2018 | Helgeson et al. | |
| 10,143,394 B2 | 12/2018 | Solis | |
| 10,322,261 B2 | 6/2019 | Pai et al. | |
| 10,362,952 B2 | 7/2019 | Basu et al. | |
| 10,362,954 B2 | 7/2019 | de la Rama et al. | |
| 10,376,170 B2 | 8/2019 | Quinn et al. | |
| 10,384,036 B2 | 8/2019 | Romoscanu | |
| 10,398,500 B2 | 9/2019 | Huszar et al. | |
| 10,441,449 B1 * | 10/2019 | Longo | A61F 2/966 |
| 10,478,325 B2 | 11/2019 | Syed | |
| 10,506,938 B2 | 12/2019 | Wu et al. | |
| 10,537,259 B2 | 1/2020 | Wu et al. | |
| 10,542,899 B2 | 1/2020 | Wu et al. | |
| 10,556,091 B2 | 2/2020 | Truhler et al. | |
| 10,575,742 B2 | 3/2020 | Wu et al. | |
| 10,575,745 B2 | 3/2020 | Solis | |
| 10,595,738 B2 | 3/2020 | Sterrett et al. | |
| 10,595,740 B2 | 3/2020 | Hoitink et al. | |
| 10,602,948 B2 | 3/2020 | Wu et al. | |
| 10,646,692 B2 | 5/2020 | Tegg et al. | |
| 10,653,423 B2 | 5/2020 | Starnes | |
| 10,702,677 B2 | 7/2020 | Okamura et al. | |
| 10,737,060 B2 | 8/2020 | Gupta et al. | |
| 10,835,712 B2 | 11/2020 | Wada | |
| 10,842,990 B2 | 11/2020 | de la Rama et al. | |
| 10,857,349 B2 | 12/2020 | de la Rama et al. | |
| 10,869,992 B2 | 12/2020 | Pai et al. | |
| 10,898,685 B2 | 1/2021 | Tegg | |
| 10,912,925 B2 | 2/2021 | Houck | |
| 10,953,196 B2 | 3/2021 | Raab et al. | |
| 10,959,636 B2 | 3/2021 | Dahlen et al. | |
| 10,966,623 B2 | 4/2021 | Wu et al. | |
| 10,966,753 B2 | 4/2021 | Coyle et al. | |
| 10,967,150 B2 | 4/2021 | Helgeson et al. | |
| 10,987,045 B2 | 4/2021 | Basu et al. | |
| 11,033,715 B2 | 6/2021 | Beeckler et al. | |
| 11,039,772 B2 | 6/2021 | Wu et al. | |
| 11,039,773 B2 | 6/2021 | Sterrett et al. | |
| 11,083,400 B2 | 8/2021 | Hoitink et al. | |

(56) References Cited

U.S. PATENT DOCUMENTS

| | | | |
|---|---|---|---|
| 11,116,436 B2 | 9/2021 | Wu et al. | |
| 11,116,476 B2 | 9/2021 | Buesseler et al. | |
| 11,141,568 B2 | 10/2021 | Hsueh et al. | |
| 11,160,482 B2 | 11/2021 | Solis | |
| 11,172,858 B2 | 11/2021 | Olson et al. | |
| 11,272,886 B2 | 3/2022 | Harlev et al. | |
| 2001/0023348 A1* | 9/2001 | Ashley | A61B 18/148 606/41 |
| 2002/0165484 A1 | 11/2002 | Bowe et al. | |
| 2004/0193032 A1* | 9/2004 | Mogul | A61M 25/0147 600/374 |
| 2012/0253161 A1 | 10/2012 | Harlev et al. | |
| 2014/0100639 A1 | 4/2014 | Lee et al. | |
| 2014/0114307 A1* | 4/2014 | Moisa | A61B 5/287 606/41 |
| 2014/0257069 A1* | 9/2014 | Eliason | A61B 18/1492 600/373 |
| 2014/0257296 A1 | 9/2014 | Morgenstern et al. | |
| 2014/0276613 A1* | 9/2014 | Goodman | A61B 18/1492 604/95.04 |
| 2015/0119911 A1 | 4/2015 | Mckenzie | |
| 2015/0366508 A1 | 12/2015 | Chou et al. | |
| 2016/0213423 A1 | 7/2016 | Kauphusman et al. | |
| 2016/0278851 A1 | 9/2016 | Mannion et al. | |
| 2016/0331933 A1 | 11/2016 | Knutsen | |
| 2016/0346040 A1 | 12/2016 | Hall et al. | |
| 2017/0281268 A1 | 10/2017 | Tran et al. | |
| 2017/0319269 A1 | 11/2017 | Oliverius et al. | |
| 2017/0367756 A1 | 12/2017 | Sliwa et al. | |
| 2018/0042667 A1 | 2/2018 | Pappone et al. | |
| 2018/0085064 A1 | 3/2018 | Auerbach et al. | |
| 2018/0161093 A1* | 6/2018 | Basu | A61B 18/1492 |
| 2018/0229030 A1 | 8/2018 | Dubuclet et al. | |
| 2018/0279994 A1* | 10/2018 | Schaer | A61B 8/0883 |
| 2018/0369574 A1 | 12/2018 | Dubuclet et al. | |
| 2019/0009052 A1 | 1/2019 | Oliverius et al. | |
| 2019/0125378 A1 | 5/2019 | Shelton, IV et al. | |
| 2019/0192826 A1 | 6/2019 | Wada | |
| 2020/0121894 A1 | 4/2020 | Prabhu et al. | |
| 2020/0138378 A1 | 5/2020 | De La Rama et al. | |
| 2020/0214635 A1 | 7/2020 | Dahlen et al. | |
| 2020/0253496 A1 | 8/2020 | Deno et al. | |
| 2020/0405166 A1 | 12/2020 | Wu et al. | |
| 2021/0145342 A1 | 5/2021 | Wang | |
| 2021/0187246 A1 | 6/2021 | Houck | |
| 2021/0204871 A1 | 7/2021 | Goedeke et al. | |
| 2021/0268234 A1 | 9/2021 | Helgeson et al. | |
| 2021/0298656 A1 | 9/2021 | Wu et al. | |
| 2021/0361216 A1 | 11/2021 | Hoitink et al. | |
| 2021/0401345 A1 | 12/2021 | Wu et al. | |
| 2022/0023594 A1 | 1/2022 | Pai | |
| 2022/0054066 A1 | 2/2022 | Solis | |
| 2022/0061727 A1 | 3/2022 | Olson et al. | |

FOREIGN PATENT DOCUMENTS

| | | | |
|---|---|---|---|
| CN | 103930153 | A | 7/2014 |
| CN | 101927053 | B | 1/2015 |
| CN | 104287824 | A | 1/2015 |
| CN | 103157168 | B | 4/2015 |
| CN | 106562820 | A | 4/2017 |
| CN | 106859765 | A | 6/2017 |
| CN | 206880930 | U | 1/2018 |
| CN | 104958824 | B | 12/2018 |
| CN | 104434083 | B | 4/2019 |
| CN | 104968261 | B | 5/2019 |
| CN | 105592778 | B | 7/2019 |
| CN | 110536646 | A | 12/2019 |
| CN | 111225627 | A | 6/2020 |
| CN | 111432739 | A | 7/2020 |
| CN | 111657866 | A | 9/2020 |
| CN | 106264715 | B | 11/2020 |
| CN | 106264716 | B | 11/2020 |
| CN | 106308790 | B | 6/2021 |
| CN | 107529958 | B | 7/2021 |
| CN | 109310469 | B | 7/2021 |
| CN | 109641121 | B | 9/2021 |
| CN | 109952123 | B | 9/2021 |
| CN | 110545874 | B | 9/2021 |
| CN | 110559544 | B | 9/2021 |
| CN | 113425304 | A | 9/2021 |
| CN | 105615994 | B | 10/2021 |
| CN | 109963610 | B | 11/2021 |
| CN | 108289709 | B | 3/2022 |
| EP | 0889744 | B1 | 1/2004 |
| EP | 1484077 | A2 | 12/2004 |
| EP | 1254641 | B1 | 11/2008 |
| EP | 1690564 | B1 | 4/2009 |
| EP | 1723981 | B1 | 8/2010 |
| EP | 2135634 | B1 | 10/2011 |
| EP | 2018203 | B1 | 6/2012 |
| EP | 1814450 | B1 | 1/2013 |
| EP | 2269532 | B1 | 3/2013 |
| EP | 2604306 | B1 | 1/2014 |
| EP | 2915555 | A1 | 9/2015 |
| EP | 3053517 | A1 | 8/2016 |
| EP | 1968679 | B1 | 9/2016 |
| EP | 2241279 | B1 | 9/2016 |
| EP | 3123972 | A1 | 2/2017 |
| EP | 3141185 | A1 | 3/2017 |
| EP | 3115076 | A4 | 10/2017 |
| EP | 3117863 | A4 | 10/2017 |
| EP | 3111871 | B1 | 3/2018 |
| EP | 3111872 | B1 | 4/2018 |
| EP | 3057488 | B1 | 5/2018 |
| EP | 2848226 | B1 | 7/2018 |
| EP | 3363397 | A1 | 8/2018 |
| EP | 3391928 | A1 | 10/2018 |
| EP | 3122276 | B1 | 11/2018 |
| EP | 3398549 | A1 | 11/2018 |
| EP | 1759668 | B1 | 12/2018 |
| EP | 3037122 | B1 | 12/2018 |
| EP | 2234537 | B1 | 1/2019 |
| EP | 2569040 | B1 | 2/2019 |
| EP | 3023052 | B1 | 3/2019 |
| EP | 3466363 | A1 | 4/2019 |
| EP | 2550989 | B1 | 6/2019 |
| EP | 3512589 | A1 | 7/2019 |
| EP | 3512590 | A1 | 7/2019 |
| EP | 3527125 | A1 | 8/2019 |
| EP | 3531903 | A1 | 9/2019 |
| EP | 3434218 | B1 | 2/2020 |
| EP | 2908723 | B1 | 3/2020 |
| EP | 3114987 | B1 | 8/2020 |
| EP | 3178516 | B1 | 9/2020 |
| EP | 3738508 | A1 | 11/2020 |
| EP | 3738509 | A1 | 11/2020 |
| EP | 3340916 | B1 | 12/2020 |
| EP | 3579908 | B1 | 12/2020 |
| EP | 3750475 | A1 | 12/2020 |
| EP | 2155301 | B1 | 4/2021 |
| EP | 3432820 | B1 | 4/2021 |
| EP | 3476331 | B1 | 5/2021 |
| EP | 3579758 | B1 | 5/2021 |
| EP | 2809254 | B1 | 6/2021 |
| EP | 3508245 | B1 | 7/2021 |
| EP | 3858277 | A1 | 8/2021 |
| EP | 3892221 | A1 | 10/2021 |
| EP | 3932343 | A4 | 1/2022 |
| EP | 3791820 | B9 | 4/2022 |
| IN | 201614021431 | A | 12/2016 |
| IN | 201614021450 | A | 12/2016 |
| JP | 11332870 | A | 12/1999 |
| JP | 4545384 | B2 | 7/2010 |
| JP | 2010535546 | A | 11/2010 |
| JP | 4887810 | B2 | 2/2012 |
| JP | 4940332 | B2 | 3/2012 |
| JP | 2012055602 | A | 3/2012 |
| JP | 2012200509 | A | 10/2012 |
| JP | 5154031 | B2 | 2/2013 |
| JP | 5193190 | B2 | 5/2013 |
| JP | 5372314 | B2 | 12/2013 |
| JP | 2014014713 | A | 1/2014 |

(56) References Cited

FOREIGN PATENT DOCUMENTS

| | | |
|---|---|---|
| JP | 2014506171 A | 3/2014 |
| JP | 5550150 B2 | 5/2014 |
| JP | 5762697 B2 | 6/2015 |
| JP | 5856712 B2 | 2/2016 |
| JP | 5908270 B2 | 4/2016 |
| JP | 2016511026 A | 4/2016 |
| JP | 5944331 B2 | 7/2016 |
| JP | 6050522 B2 | 12/2016 |
| JP | 2017051211 A | 3/2017 |
| JP | 2017104552 A | 6/2017 |
| JP | 6246742 B2 | 12/2017 |
| JP | 6342524 B2 | 6/2018 |
| JP | 6434495 B2 | 12/2018 |
| JP | 6445509 B2 | 12/2018 |
| JP | 6445742 B1 | 12/2018 |
| JP | 6466114 B2 | 2/2019 |
| JP | 6515084 B2 | 4/2019 |
| JP | 6528010 B1 | 5/2019 |
| JP | 6655655 B2 | 2/2020 |
| JP | 6776025 B2 | 10/2020 |
| JP | 6821812 B2 | 1/2021 |
| JP | 2021007772 A | 1/2021 |
| JP | 2021501011 A | 1/2021 |
| JP | 6843502 B2 | 3/2021 |
| JP | 6894004 B2 | 6/2021 |
| JP | 6920312 B2 | 8/2021 |
| JP | 6926306 B2 | 8/2021 |
| JP | 6932484 B2 | 8/2021 |
| JP | 6936872 B2 | 9/2021 |
| JP | 6980386 B2 | 11/2021 |
| JP | 2022020838 A | 2/2022 |
| RU | 2016124794 A | 12/2017 |
| RU | 2016125763 A | 1/2018 |
| WO | WO-9421168 A1 * | 9/1994 ......... A61B 18/1492 |
| WO | 9843530 A1 | 10/1998 |
| WO | 0168178 A1 | 9/2001 |
| WO | 2008091197 A1 | 7/2008 |
| WO | 2012092016 A1 | 7/2012 |
| WO | 2014124231 A1 | 8/2014 |
| WO | 2015089649 A1 | 6/2015 |
| WO | WO-2016130442 A1 * | 8/2016 ......... A61B 1/00066 |
| WO | 2017098198 A1 | 6/2017 |
| WO | 2018136741 A1 | 1/2018 |
| WO | 2018053148 A1 | 3/2018 |
| WO | 2018053164 A1 | 3/2018 |

* cited by examiner

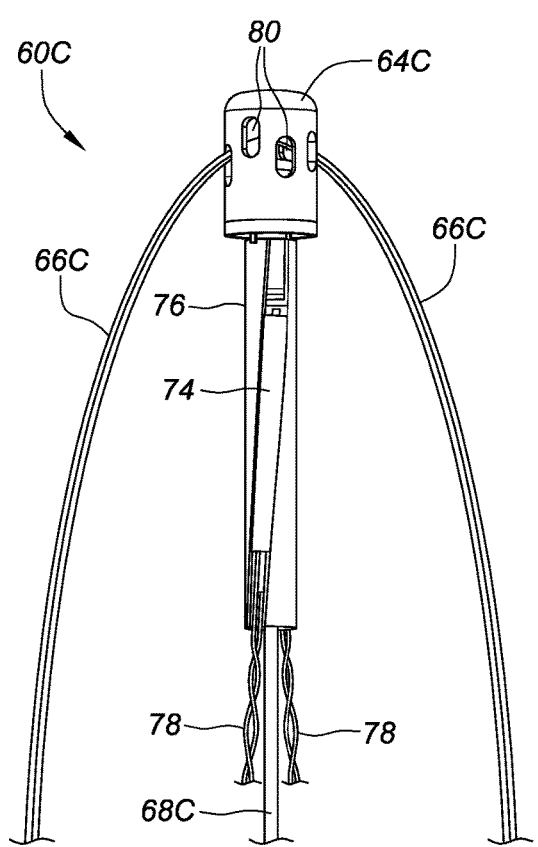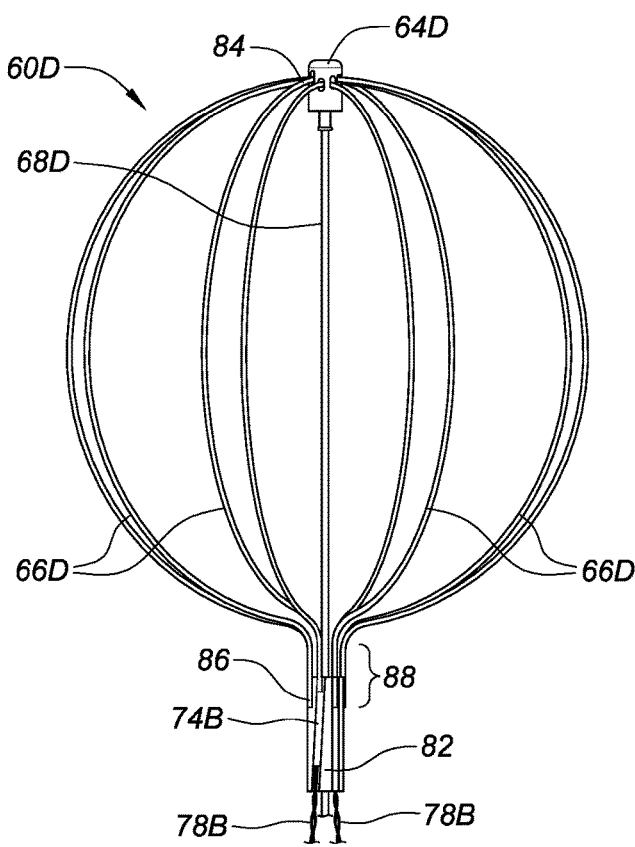
FIG. 4          FIG. 5A
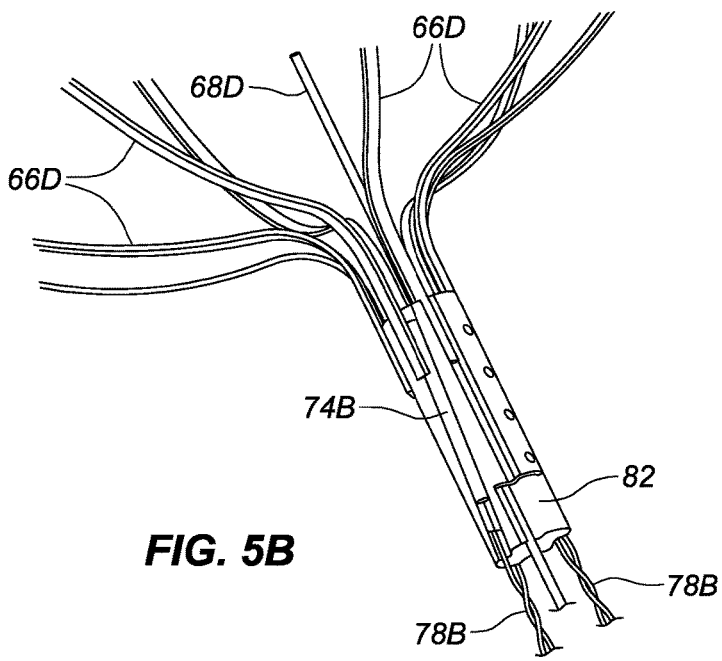
FIG. 5B

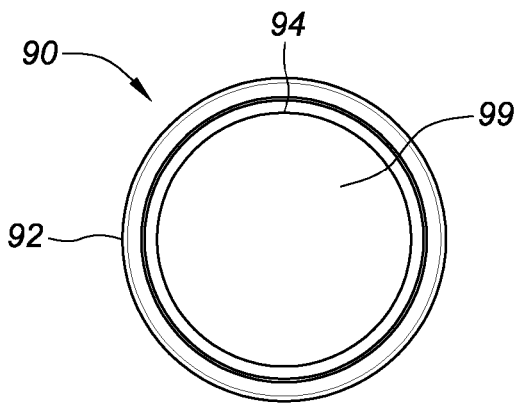
FIG. 6A
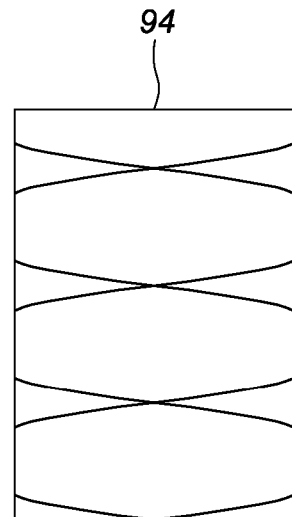
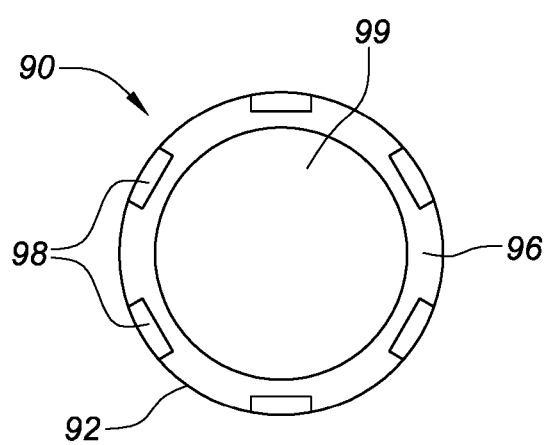
FIG. 6C
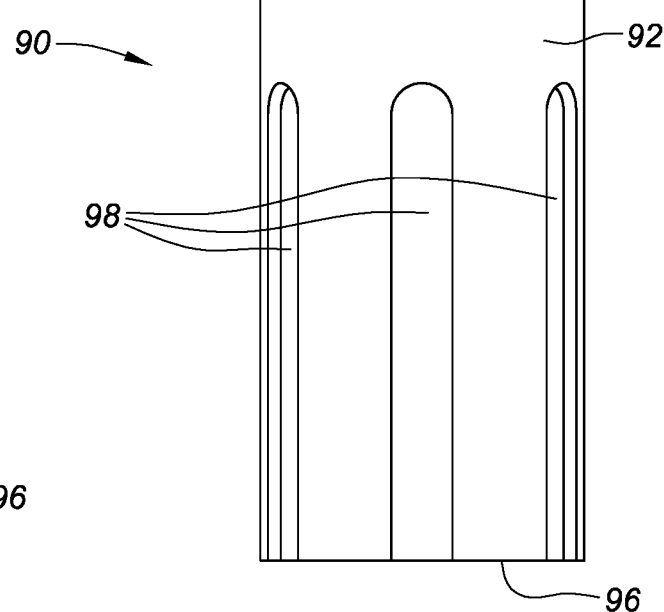
FIG. 6B

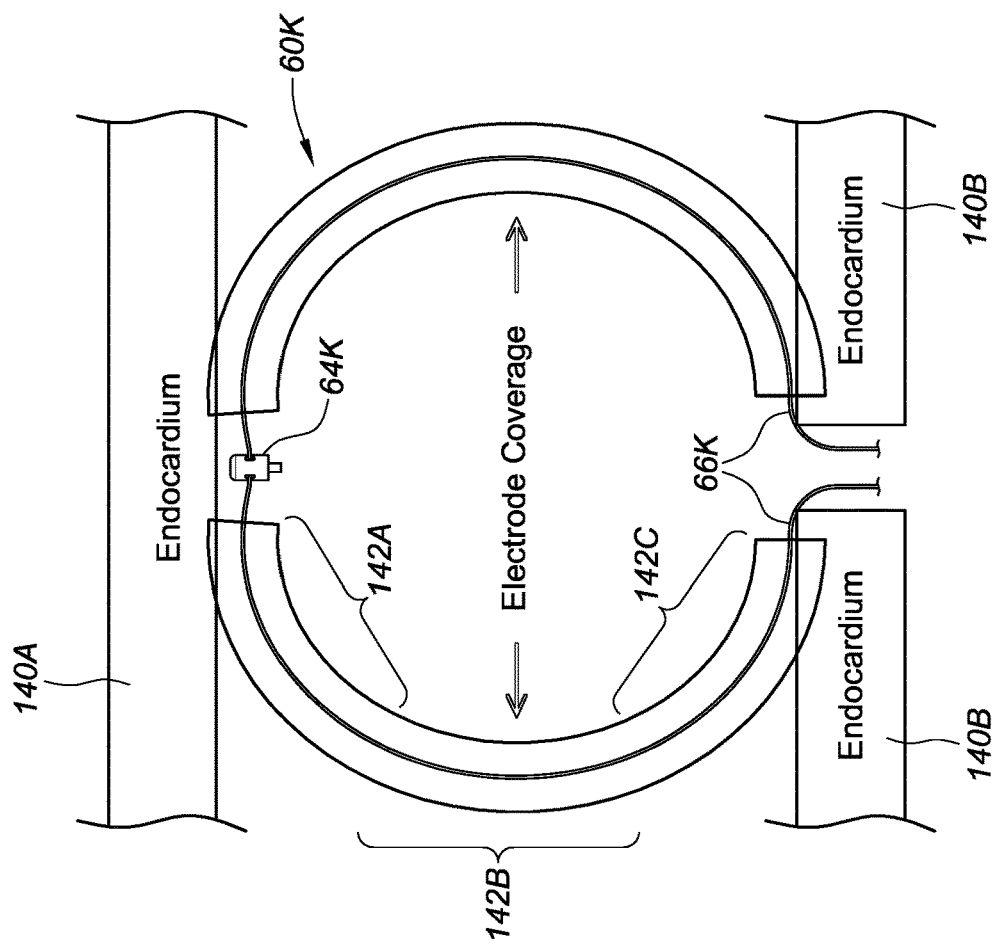
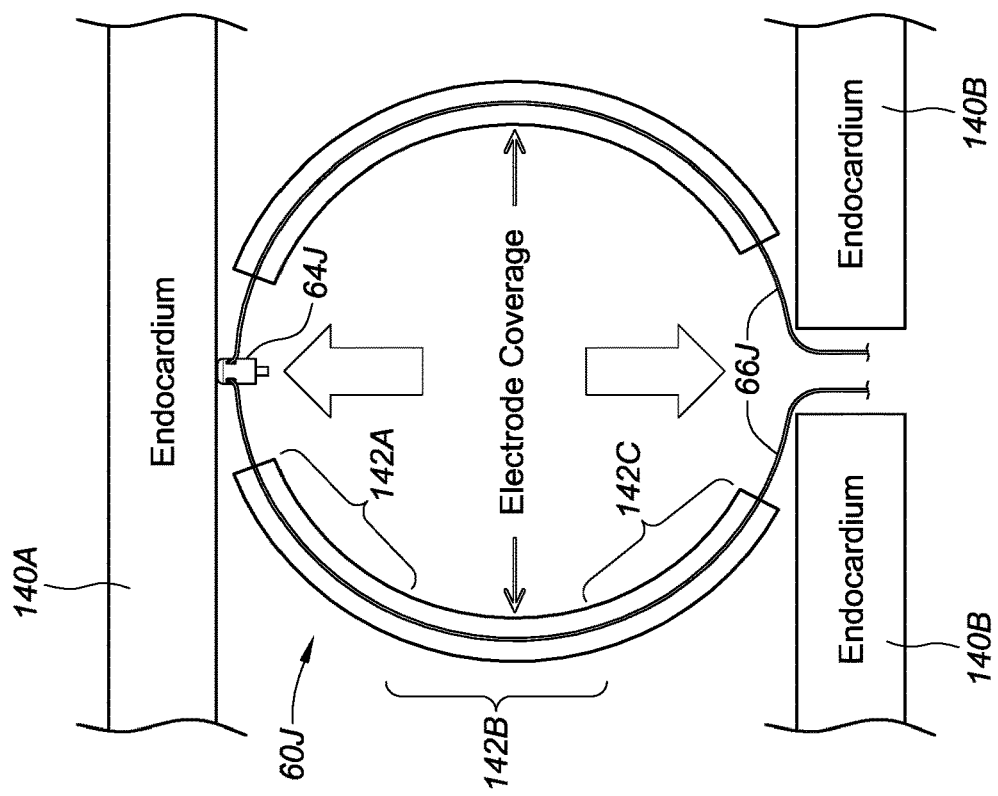

CONTROLLABLE EXPANDABLE CATHETER

CROSS-REFERENCE TO RELATED APPLICATIONS

This application is a U.S. National Stage of PCT/US2018/062865 filed Nov. 28, 2018; which claims the benefit of U.S. provisional application No. 62/743,389, filed 9 Oct. 2018 (the '389 application) and this application claims the benefit of U.S. provisional application No. 62/591,278, filed 28 Nov. 2017 (the '278 application). The '389 application and the '278 application are both hereby incorporated by reference as though fully set forth herein.

BACKGROUND a. Field

This disclosure relates to systems and apparatuses for catheter-based cardiac electrophysiology mapping and-therapy. In particular, the instant disclosure relates to controllable expandable basket catheters for mapping and therapy.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other therapies and/or treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

To position a catheter at a desired site within the body, some type of navigation may be used, such as using mechanical steering features incorporated into the catheter (or an introducer). In some examples, medical personnel may manually manipulate and/or operate the catheter using the mechanical steering features.

In order to facilitate the advancement of catheters through a patient's vasculature, a navigating system may be used. Such navigating systems may include, for example, electric-field-based positioning and navigating systems that are able to determine the position and orientation of the catheter (and similar devices) within the body and map features of the body. Various therapies can be delivered by the catheter to tissue with varied shapes and sizes. To better accommodate variations in tissue configurations and to provide sufficient contact with the tissue for therapy, it can be important to have multiple sensors coupled with flexible spline elements on structures such as distal basket configurations to map the tissue and/or to contact the tissue for therapy. The ability to vary the stiffness of the flexible spline elements can allow for more useful configurations of the baskets or other flexible structures (e.g., more contact with tissue for treatment, etc.).

The foregoing discussion is intended only to illustrate the present field and should not be taken as disavowal of claim scope.

BRIEF SUMMARY

The instant disclosure, in at least one embodiment, comprises an expandable structure with an expandable configuration and a collapsed configuration, a handle, operably coupled to the expandable structure; the handle further including a selective movement limiter, and a deflection control member coupled with the distal hub, where the deflection control member is configured to adjust a stiffness of the expandable structure, from a first stiffness to a second stiffness, and maintain the first stiffness or the second stiffness when the selective movement limiter couples with the deflection control member and limits a longitudinal movement of the deflection control member, wherein the deflection control member is configured to move freely when the selective movement limiter is not coupled with the deflection control member.

In another embodiment, a method of using a catheter with an expandable structure can comprise placing the catheter with the expandable structure in an undeployed shape in a body, where the expandable structure comprises a plurality of splines; deploying the expandable structure from the undeployed shape to a deployed shape, where the expandable structure has a first stiffness; and adjusting the stiffness of the expandable structure, using a deflection control member, from the first stiffness to a second stiffness.

In another embodiment, a system comprising: a basket, where the basket comprises a plurality of splines where each has a spline proximal end and a spline distal end; a distal hub, where each of the spline distal ends is coupled with the distal hub; a magnetic sensor; a deflection control member coupled with the distal hub, where the deflection control member is configured to adjust a stiffness of the basket, from a first stiffness to a second stiffness, and maintain the first stiffness or the second stiffness; a clamping mechanism where the clamping mechanism engages the deflection control member and limits a longitudinal movement of the deflection control member

BRIEF DESCRIPTION OF THE DRAWINGS

FIG. 4 is a side view of a distal portion of a catheter including a basket comprising multiple splines including two magnetic sensors positioned in a distal location of the basket, in accordance with embodiments of the present disclosure.

FIG. 5A is a side view of a distal end portion of a distal portion of a catheter including a basket comprising a plurality of splines including two magnetic sensors positioned at a proximal location of the basket, in accordance with embodiments of the present disclosure.

FIG. 5B is a side view of the distal end portion of the catheter of FIG. 4A including the two magnetic sensors positioned at the proximal location of the basket, in accordance with embodiments of the present disclosure.

FIGS. 6A-C show a coupler, in accordance with embodiments of the present disclosure. FIG. 6A is a cross-sectional view of a proximal end of the coupler. FIG. 6B is a side view of the coupler. FIG. 6C is a cross-sectional view of the distal end of the coupler.

FIG. 9A shows the clamping mechanism in a first position and FIG. 9B shows the clamping mechanism in a second position, in accordance with embodiments of the present disclosure.

FIG. 12A is a side view of two splines for a catheter where each of the two splines have a first spline shape, in accordance with embodiments of the present disclosure.

FIG. 12B is a side view of two splines for a catheter with a second spline shape for increased contact between proximal portions of the splines and tissue, in accordance with embodiments of the present disclosure.

DETAILED DESCRIPTION OF EMBODIMENTS

Figure 1:
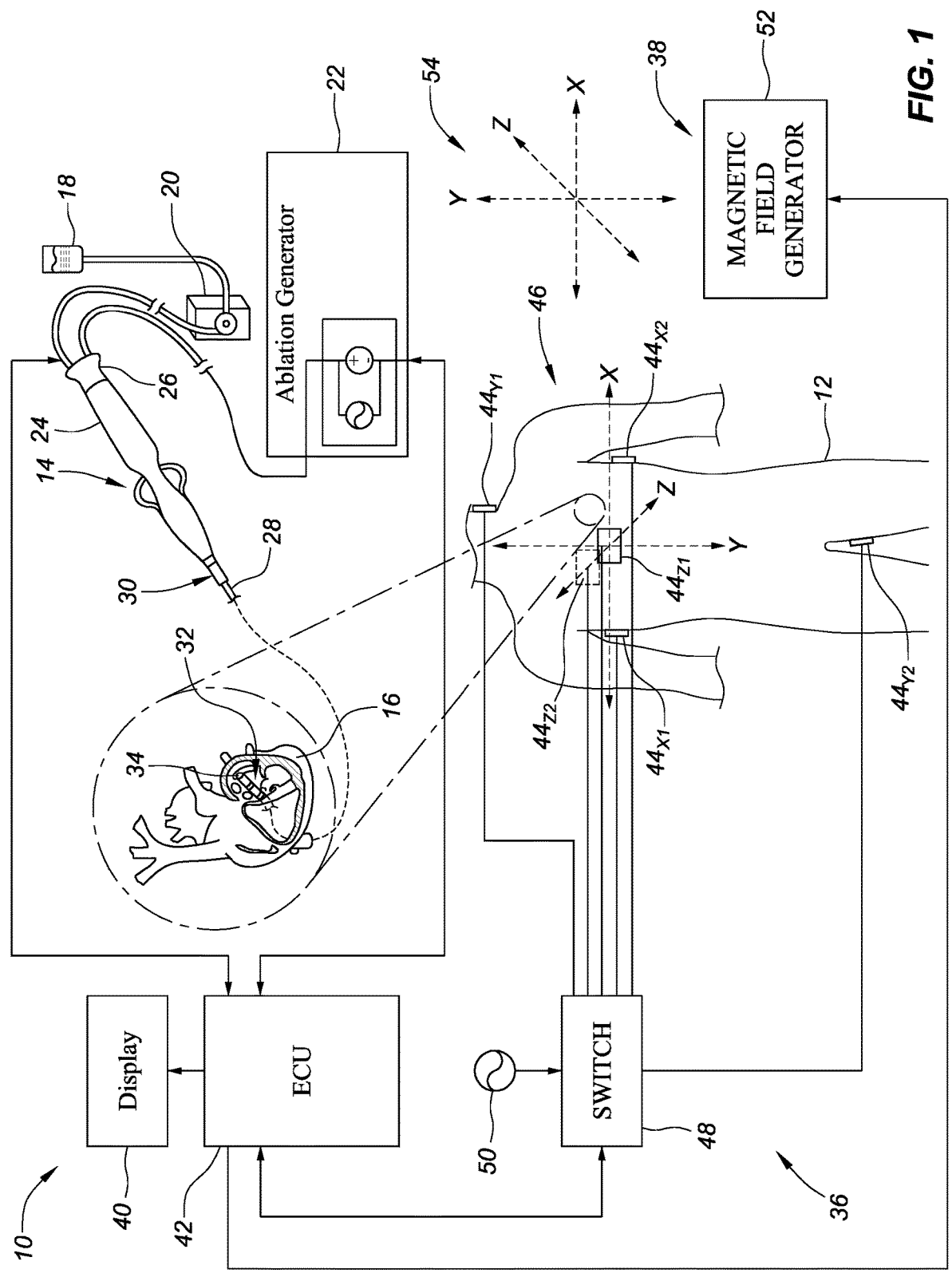
FIG. 1 is a system diagram showing a medical device and a medical positioning system, in accordance with embodiments of the present disclosure.

Referring now to the figures, in which like reference numerals refer to the same or similar features in the various views, FIG. 1 illustrates one embodiment of a system 10 for navigating a medical device within a body 12. In the illustrated embodiment, the medical device comprises a catheter 14 that is shown schematically entering a heart that has been exploded away from the body 12. The catheter 14, in this embodiment, is depicted as an irrigated radiofrequency (RF) ablation catheter for use in the treatment of cardiac tissue 16 in the body 12. It should be understood, however, that the system 10 may find application in connection with a wide variety of medical devices used within the body 12 for diagnosis or treatment. For example, the system 10 may be used to navigate, for example, an electrophysiological catheter, a mapping catheter, an intracardiac echocardiography (ICE) catheter, or an ablation catheter using a different type of ablation energy (e.g., cryoablation, ultrasound, etc.). Further, it should be understood that the system 10 may be used to navigate medical devices used in the diagnosis or treatment of portions of the body 12 other than cardiac tissue 16. Further description of the systems and components are contained in U.S. patent application Ser. No. 13/839,963 filed on 15 Mar. 2013, which is hereby incorporated by reference in its entirety as though fully set forth herein.

Referring still to FIG. 1, the ablation catheter 14 is connected to a fluid source 18 for delivering a biocompatible irrigation fluid such as saline through a pump 20, which may comprise, for example, a fixed rate roller pump or variable volume syringe pump with a gravity feed supply from fluid source 18 as shown. The catheter 14 is also electrically connected to an ablation generator 22 for delivery of RF energy. The catheter 14 may include a handle 24; a cable connector or interface 26 at a proximal end of the handle 24; and a shaft 28 having a proximal end 30, a distal end 32, and one or more electrodes 34. The connector 26 provides mechanical, fluid, and electrical connections for conduits or cables extending from the pump 20 and the ablation generator 22. The catheter 14 may also include other conventional components not illustrated herein such as a temperature sensor, additional electrodes, and corresponding conductors or leads.

The handle 24 provides a location for the physician to hold the catheter 14 and may further provide means for steering or guiding the shaft 28 within the body 12. For example, the handle 24 may include means to change the length of one or more pull wires extending through the catheter 14 from the handle 24 to the distal end 32 of shaft 28. The construction of the handle 24 may vary.

The shaft 28 may be made from conventional materials such as polyurethane and may define one or more lumens configured to house and/or transport electrical conductors, fluids, or surgical tools. The shaft 28 may be introduced into a blood vessel or other structure within the body 12 through a conventional introducer. The shaft 28 may then be steered or guided through the body 12 to a desired location such as the tissue 16 using guide wires or pull wires or other means known in the art including remote control guidance systems. The shaft 28 may also permit transport, delivery, and/or removal of fluids (including irrigation fluids and bodily fluids), medicines, and/or surgical tools or instruments. It should be noted that any number of methods can be used to introduce the shaft 28 to areas within the body 12. This can include introducers, sheaths, guide sheaths, guide members, guide wires, or other similar devices. For ease of discussion, the term introducer will be used throughout.

The system 10 may include an electric-field-based positioning system 36, a magnetic-field-based positioning system 38, a display 40, and an electronic control unit (ECU) 42 (e.g., a processor). Each of the exemplary system components is described further below.

The electric-field-based positioning system 36 and the magnetic-field-based positioning system 38 are provided to determine the position and orientation of the catheter 14 and similar devices within the body 12. The position and orientation of the catheter 14 and similar devices within the body 12 can be determined by the system 36 and/or the system 38. The system 36 may comprise, for example, the EnSite™ NavX™ system sold by St. Jude Medical, Inc. of St. Paul, Minn., and described in, for example, U.S. Pat. No. 7,263,397 titled "Method and Apparatus for Catheter Navigation and Location Mapping in the Heart," the entire disclosure of which is hereby incorporated by reference as though fully set forth herein. The systems 36 and 38 may comprise, for example, the EnSite Precision™ system sold by St. Jude Medical, Inc., of St. Paul, Minn. The system 36 operates based upon the principle that when low amplitude electrical signals are passed through the thorax, the body 12 acts as a voltage divider (or potentiometer or rheostat) such that the electrical potential or field strength measured at one or more electrodes 34 on the catheter 14 may be used to determine the position of the electrodes, and, therefore, of the catheter 14, relative to a pair of external patch electrodes using Ohm's law and the relative location of a reference electrode (e.g., in the coronary sinus).

In the configuration is shown in FIG. 1, the electric-field-based positioning system 36 further includes three pairs of patch electrodes 44, which are provided to generate electrical signals used in determining the position of the catheter 14 within a three-dimensional coordinate system 46. The electrodes 44 may also be used to generate EP data regarding the tissue 16. To create axes-specific electric fields within body 12, the patch electrodes are placed on opposed surfaces of the body 12 (e.g., chest and back, left and right sides of the thorax, and neck and leg) and form generally orthogonal x, y, and z axes. A reference electrode/patch (not shown) is typically placed near the stomach and provides a reference value and acts as the origin of the coordinate system 46 for the navigation system.

In accordance with this exemplary system 36 as depicted in FIG. 1, the patch electrodes include right side patch $44_{X1}$, left side patch $44_{X2}$, neck patch $44_{Y1}$, leg patch $44_{Y2}$, chest patch $44_{Z1}$, and back patch $44_{Z2}$; and each patch electrode is connected to a switch 48 (e.g., a multiplex switch) and a signal generator 50. The patch electrodes $44_{X1}$, $44_{X2}$ are placed along a first (x) axis; the patch electrodes $44_{Y1}$, $44_{Y2}$ are placed along a second (y) axis, and the patch electrodes $44_{Z1}$, $44_{Z2}$ are placed along a third (z) axis. Sinusoidal currents are driven through each pair of patch electrodes, and voltage measurements for one or more position sensors (e.g., ring electrodes 34 or a tip electrode located near the distal end 32 of catheter shaft 28) associated with the catheter 14 are obtained. The measured voltages are a function of the distance of the position sensors from the patch electrodes. The measured voltages are compared to the potential at the reference electrode and a position of the position sensors within the coordinate system 46 of the navigation system is determined.

The magnetic-field-based positioning system 38 in this exemplary embodiment employs magnetic fields to detect the position and orientation of the catheter 14 within the body 12. The system 38 may include the GMPS system made available by MediGuide, Ltd. and generally shown and described in, for example, U.S. Pat. No. 7,386,339 titled "Medical Imaging and Navigation System," the entire disclosure of which is hereby incorporated by reference as though fully set forth herein. In such a system, a magnetic field generator 52 may be employed having three orthogonally arranged coils (not shown) to create a magnetic field within the body 12 and to control the strength, orientation, and frequency of the field. The magnetic field generator 52 may be located above or below the patient (e.g., under a patient table) or in another appropriate location. Magnetic fields are generated by the coils and current or voltage measurements for one or more position sensors (not shown) associated with the catheter 14 are obtained. The measured currents or voltages are proportional to the distance of the sensors from the coils, thereby allowing determination of a position of the sensors within a coordinate system 54 of system 38.

The display 40 is provided to convey information to a physician to assist in diagnosis and treatment. The display 40 may comprise one or more conventional computer monitors or other display devices. The display 40 may present a graphical user interface (GUI) to the physician. The GUI may include a variety of information including, for example, an image of the geometry of the tissue 16, electrophysiology data associated with the tissue 16, graphs illustrating voltage levels over time for various electrodes 34, and images of the catheter 14 and other medical devices and related information indicative of the position of the catheter 14 and other devices relative to the tissue 16.

The ECU 42 provides a means for controlling the operation of various components of the system 10, including the catheter 14, the ablation generator 22, and magnetic generator 52 of the magnetic-field-based positioning system 38. The ECU 42 may also provide a means for determining the geometry of the tissue 16, electrophysiology characteristics of the tissue 16, and the position and orientation of the catheter 14 relative to tissue 16 and the body 12. The ECU 42 also provides a means for generating display signals used to control the display 40.

As the catheter 14 moves within the body 12, and within the electric field generated by the electric-field-based positioning system 36, the voltage readings from the electrodes 34 change, thereby indicating the location of catheter 14 within the electric field and within the coordinate system 46 established by the system 36. The ring electrodes 34 communicate position signals to ECU 42 through a conventional interface (not shown).

Figure 2:
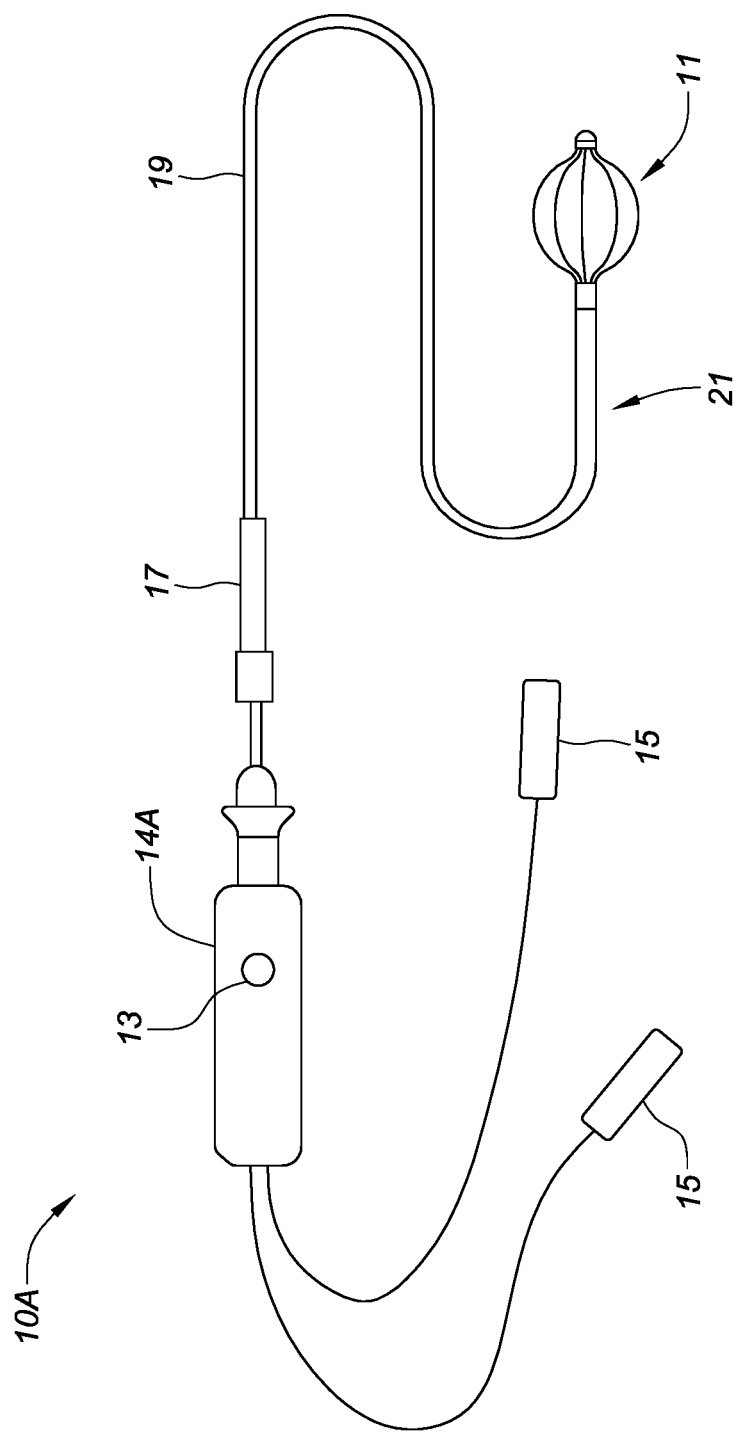
FIG. 2 is a diagrammatic view of a catheter system that is designed to perform one or more diagnostic and/or therapeutic functions, in accordance with embodiments of the present disclosure.

FIG. 2 is a diagrammatic view of a catheter system 10A employing an expandable structure 11 in accordance with an embodiment of the present teachings. Catheter system 10A includes an actuator 13 that is part of a handle 14A and connectors 15 disposed proximal to handle 14A for making electrical connections to a visualization, navigation, and/or mapping system (not shown) such as those systems available under the brand name Ensite™ NavX™ (aka Ensite™ "Classic" as well as newer versions of the Ensite™ system, denoted as Ensite™ Velocity™) and available from St. Jude Medical, Inc. Handle 14A can have a uni-directional design, a bi-directional design, or any other suitable design and be accordingly configured to steer the expandable structure 11, as discussed in more detail in commonly assigned U.S. Pat. No. 8,676,290, the entire disclosure of which is incorporated herein by reference. The actuator 13 (e.g., button, lever, knob, etc.) can be used to engage a control element for controlling features of the expandable structure 11 (e.g., size, shape, stiffness, etc.).

Catheter system 10A can also include an introducer 17 located distally of handle 14A that may be used to deliver an elongated catheter body 19 into the body of a patient, through a hemostasis valve of another longer introducer, for example. Elongated catheter body 19 can extend from introducer 17. Elongated catheter body 19 can comprise an elongated tubular construction having one or more lumens. Elongated catheter body 19 can be flexible or bendable. Elongated catheter body 19 can be of any suitable construction and made of any suitable material as known to those of ordinary skill in the art. Elongated catheter body 19 can have any outer diameter, but may generally be configured for insertion into the vasculature of a body of a patient and, in some embodiments, be less than about 8 French. Elongated catheter body 19 can have an outer wall of any thickness, but may generally be configured so that one or more lumens can be disposed within elongated catheter body 19 to accommodate pull wires, lead wires, sensor cables, and any other wires, cable, and/or tubes that may be needed in particular applications. Handle 14A, connectors 15, introducer 17, and elongated catheter body 19 can be readily modified as dictated by the aesthetic or functional needs of particular applications.

Expandable structure 11 is configured to extend from a distal portion 21 of elongated catheter body 19. Although expandable structure 11 is described and illustrated in connection with an intracardiac catheter system 10A, expandable structure 11 may be utilized in connection with other types of medical devices, such as for example and without limitation, stone retrieval baskets, distal protection devices, renal artery ablation devices, snares, and other retrieval devices. As discussed in further detail below in connection with FIGS. 3A-5B and 8A-8B, expandable structure 11 may be configured to support electrodes and to be radially outwardly expandable and inwardly collapsible FIG. 3A an isometric view of a distal end portion of an elongate medical device with a basket including a plurality of ring electrodes, in accordance with embodiments of the present disclosure. An elongate medical device 60A (i.e., a catheter 60A) can include a basket 62A that is located at a distal end portion of the elongate medical device 60A. The basket 62A can comprise a distal hub 64A and a plurality of splines 66A and a deflection control member 68A. Each of the plurality of splines 66A can include a plurality of interactive elements 70A, where $70A_x$ can represent individual interactive elements in the plurality of interactive elements $70A_1$, $70A_2$, $70A_3$, . . . etc. as shown in the exemplary configuration of FIG. 3A.

The interactive elements can include, for example, electrodes, energy delivery elements, thermocouples, force sensors (to register, for example, tissue contact and/or total force exerted on tissue), strain gauges, strain sensors, position sensors, biosensors (e.g., sensors capable of converting a biological response to an electrical signal), diagnostic sensors, therapy sensors, chemical sensors (e.g., capable of delivery and or monitoring of drugs/chemicals, etc.), light-emitting sensors, acoustic sensors, ultrasound sensors, energy receiving and/or measuring sensors, a magnetic coil or sensor, thermoelectric elements, or other sensors. The interactive elements can be electrically connected (e.g., a plurality of conductive electrical traces, wires, etc.) to a power supply, controller (e.g., ECU 42 of FIG. 1), an ablation generator (e.g., the ablation generator 22 of FIG. 1), a positioning system 36 and/or 38 of FIG. 1) or other device used to, for example, delivery therapy, generate, amplify, receive, and/or process a signal.

Spacing of the plurality of interactive elements 70A can be equal or unequal. For example, in some embodiments, the plurality of interactive elements 70A can all have an equal distance between each of the plurality of interactive elements 70A (e.g., 1 mm between each electrode). In other embodiments, the spacing can vary between the plurality of interactive elements 70A (e.g., 1 mm between some of the plurality of electrodes 70A and 2 mm between others of the plurality of interactive elements 70A). A typical range of spacing between each of the plurality of interactive elements 70A can be approximately 0.5 mm to 2 mm. Tighter spacing (i.e., closer interactive elements, shorter/less distances between interactive elements, etc.) of the plurality of interactive elements can be used, for example, for contact mapping compared to non-contact mapping where the interactive elements can be further apart (greater/more distance between interactive elements) compared to the contact mapping arrangement).

Spacing between each of the plurality of interactive elements 70A can vary along each spline 66A and/or differ from spline to spline. For example, one embodiment (not shown) of the plurality of interactive elements 70A could have a first spacing pattern (A) on a first spline and a second spacing pattern (B) on a second spline with the spacing patterns alternating every other spline (A-B-A-B . . . ). Another example could include a third spacing pattern (C) allowing the splines/spacing patterns to have a configuration of A-B-C-A-B-C, etc. Any suitable number of spacing patterns for the plurality of interactive elements 66A is possible with any possible combination/arrangement of the splines with the different spacing patterns (e.g., A-A-A-B-B-B, etc.; A-A-B-B-C-C, etc.).

Distribution of the plurality of interactive elements 70A can also vary between embodiments. For example, one embodiment can include more of the plurality of interactive elements 70A located on the distal portion of the splines 66A and fewer of the plurality of interactive elements 70A on the proximal portion of the splines 66A (e.g., FIG. 2B). In another embodiment (not shown), a first pattern of distribution a spline 66A can have four interactive elements on a distal portion of the spline (i.e., distal spline interactive elements), four interactive elements on the equatorial portion (e.g., proximate a midpoint between the distal spline end and the proximal spline end) of the spline 66A (i.e., equatorial spline interactive elements), and four interactive elements on the proximal portion of the spline 66A (i.e., proximal spline interactive elements). Another pattern of distribution could include four interactive elements 70A on the distal and equatorial portions of the spline 66A only. Still another pattern of distribution could be four interactive elements on the distal portion of the spline 66A, four interactive elements on the equatorial portion, and two interactive elements on the proximal portion. Any suitable combination of different distribution patterns of interactive elements on the splines can be used to accommodate various physiological features in a body.

Each spline 66A can have one or more proximal spline interactive elements (not shown in FIG. 3A; see, e.g., $70_{prox}$ in FIG. 3B) located at a proximal portion of the spline 66A. The one or more proximal spline interactive elements (e.g., $70_{prox}$ can facilitate contact with tissue (e.g., heart wall such as the septum between the right atrium/left atrium at fossa crossing) proximal the proximal end portion of the basket 62A for therapy (e.g., ablation). See FIG. 3B below and related discussion for additional information.

Figure 3A:
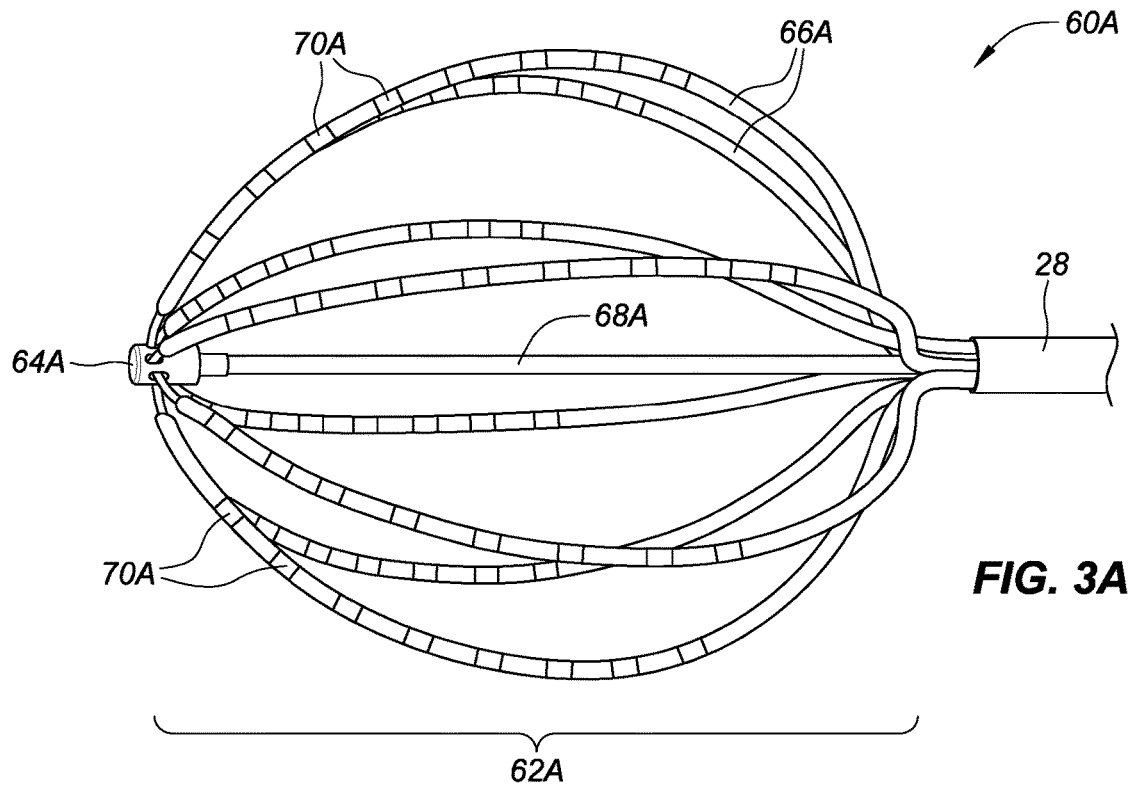
FIG. 3A is an isometric view of a distal end portion of a catheter with a basket including a plurality of ring electrodes, in accordance with embodiments of the present disclosure.
Figure 3B:
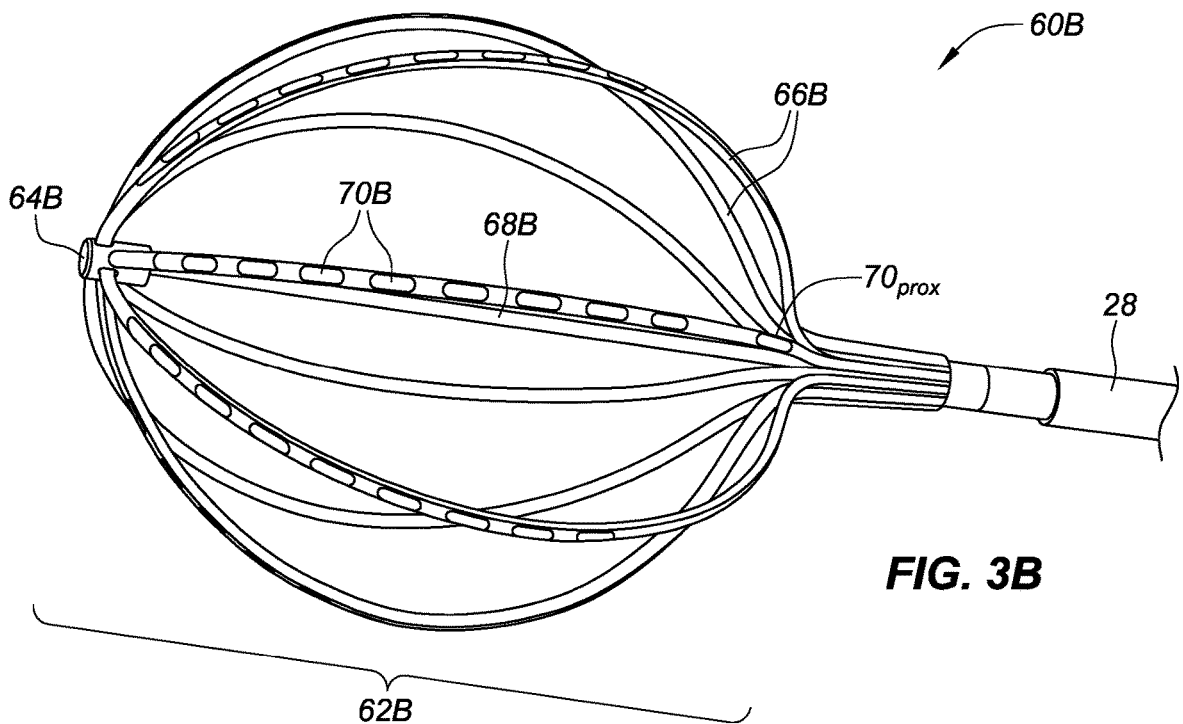
FIG. 3B is an isometric view of a catheter including a basket comprising multiple splines where one or more of the splines includes one or more electrodes located at a proximal portion of the respective spline, in accordance with embodiments of the present disclosure.

Each of the plurality of interactive elements 70A can be any suitable type of electrode. For example, a ring electrode (e.g., as shown in FIG. 3A) and/or a printed electrode (e.g., as shown in FIG. 3B). The plurality of interactive elements 70A can include a combination of electrode types (e.g., all ring electrodes, all printed electrodes, a mixture of the two, and/or other configurations/types of electrodes and/or other interactive elements). Ring electrodes can go all the way around the spline 66A (e.g., cover an entire circumference of a portion of the spline) or part of the way around the spline 66 and are typically a separate element from the spline 66A and placed on the spline 66A. Printed electrodes can be formed by, for example, depositing material onto the spline 66A by additive manufacturing, a printing process, or some other similar method. The printed electrodes can also be located on a substrate that is then placed on the spline 66A. Each of the printed electrodes can be similar to each of the ring electrodes and cover an entire circumference of a portion of the spline 66A or the printed electrode scan cover only a portion of a circumference at the portion of the spline 66A. A mixture of interactive elements types can be included on a single spline (e.g., any combination of ring electrodes and printed electrodes discussed herein can be used).

Each of the plurality of interactive elements can be any suitable size (i.e., longitudinal length, width, etc.). An embodiment can have a longitudinal length (length of the sensor as measured along a longitudinal axis of a spline) of each of the plurality of interactive elements of approximately 1 mm. Another embodiment can have a mixture of interactive elements with different longitudinal length (e.g., some interactive elements 1 mm long, other interactive elements approximately 1.5 mm long, still other interactive elements approximately 2 mm long, etc.). The longitudinal length of each interactive elements can range between approximately 0.1 mm and 5.0 mm.

The basket 62A can have a first shape and a second shape. The first shape can be an undeployed configuration that allows the basket 62A to fit inside a catheter or other elongate medical device for delivery to a location in a body. The second shape, shown in FIG. 3A, can be a deployed configuration. The deployment/undeployment of the basket 62A can be controlled by pull wires or other similar mechanisms and/or through the use of materials that are self-erecting (e.g., Nitinol). The shape of the basket 62A can vary depending on the configuration achieved using the pull wires or other deployment mechanism. The deflection control member 68 can move longitudinally, which can cause the basket 62A to change shape. The deflection control member 68 can be used to support a particular shape/configuration of the basket 62A. Additional discussion about the deflection control mechanism are found below, including with respect to FIGS. 8A-C.

The deflection control member 68A can have a deflection control member distal end 72 that can be coupled with a portion of the basket 62A (e.g., the distal hub 64A) and a deflection control member proximal end (not shown in FIG. 3A) that can be coupled with a control mechanism (e.g., a portion of the handle 24 of FIG. 1 and/or handle 14A of FIG. 2). The deflection control member 68A can be a rigid element (e.g., a tube), a semi-rigid element (e.g., a flexible tube) or a flexible element (e.g., a polymer and/or metal cable, string cord or similar element). The deflection control member 68A can include a lumen suitable for irrigation fluids (not shown). The deflection control member 68A can also include one or more irrigation ports (not shown), including ports similar to those found in U.S. application 2017/0065227, which is incorporated herein by reference in its entirety.

FIG. 3B is an isometric view of a catheter including a basket comprising multiple splines where one or more of the splines includes one or more interactive elements located at a proximal portion of the respective spline, in accordance with embodiments of the present disclosure. An elongate medical device 60B (i.e., a catheter 60B) can include a basket 62B comprising a plurality of splines 66B with one or more interactive elements 70B, including a proximal interactive elements $70_{prox}$ located at a proximal portion of the respective spline 66B. Similar to the basket 62A above (FIG. 3A), the basket 62B can also include a deflection control member (not shown) and the plurality of splines 66B can couple with a distal hub 64B.

As discussed above, the one or more interactive elements $70_{prox}$ located at a proximal portion of the one or more splines 66B and can facilitate contact with tissue (e.g., a heart wall such as the septum between the right atrium/left atrium at the fossa crossing) proximal the proximal end of the basket 62B for therapy (e.g., ablation). The exemplary interactive elements 70B shown in FIG. 3B can include printed interactive elements, although any suitable type of electrode can be used as discussed herein.

FIG. 4 is a side view of a distal portion of a catheter including a basket comprising multiple splines and two magnetic sensors positioned in a distal location of the basket, in accordance with embodiments of the present disclosure. A distal portion of a catheter 60C can include a distal hub 64C, splines 66C, and a deflection control member 68C, where the distal hub further comprises two magnetic sensors 74.

The embodiment shown in FIG. 4 includes two magnetic sensors 74 (one magnetic sensor is hidden from view in FIG. 4) in a sensor tube 76 that is connected to the distal hub 64C. The magnetic sensors 74 can have a wire pair 78 (e.g., a twisted wire pair) connected to a controller (e.g., ECU 42 of FIG. 1). The magnetic sensors 72 can allow the catheter 60C to be tracked in a mapping system (e.g., the magnetic-field-based positioning system 38 of FIG. 1). In an embodiment, position data from the catheter can be obtained using a gMPS system, commercially available from Mediguide Ltd., and generally shown and described in U.S. Pat. No. 7,386,339 entitled "Medical Imaging and Navigation System," which is incorporated herein by reference in its entirety.

The deflection control member 68C can pass through the sensor tube 76 and couple with the distal hub 64C as shown in FIG. 4. In another embodiment (not shown), the deflection control member 68 could couple with the distal hub 64C without passing through the sensor tube 76. The deflection control member 68C can be a rigid element (e.g., a tube), a semi-rigid element (e.g., a flexible tube) or a flexible element (e.g., a polymer and/or metal string or cord). Additional discussion of deflection control member movements and functions can be found below (see, e.g., FIGS. 8A-C and related discussion).

The distal hub 64C can include a plurality of spline openings 80. Each of the splines 66C can couple with distal hub 64C through one of the plurality of distal hub spline openings 80. For simplicity, the embodiment shown in FIG. 4 shows only two splines 66C connected to the distal hub 64C. Some of the plurality of distal hub spline openings 80 in FIG. 4 are open as the corresponding splines 66C are omitted. The distal hub 64C can be any suitable material (e.g., polymer, metal). The distal hub 64C can have a diameter sized to fit within an elongate medical device (e.g., a sheath or an introducer). This can allow the basket 62C to be deployed from an elongate device (e.g., the basket 62C (only a portion of which is shown in FIG. 4; see, for example, baskets 62A and 62B in FIGS. 2A-B) is pushed forward out of the elongate device and/or the elongate device is pulled back with respect to the basket 62C).

The plurality of distal hub spline openings 80 can be sized to accommodate a variety of spline sizes and/or to allow for the spline 66C to move (e.g., pivot, slide, etc.) within the distal hub spline opening 80. Each of the splines 66C may move within the spline opening 80, for example, during deployment of a basket (e.g., basket 62A, 62B of FIGS. 3A-B) and/or during adjustment of the basket shape (e.g., using the deflection control member as described herein) or other suitable times during usage of the catheter 60C.

FIG. 5A is a side view of a distal end portion of a distal portion of a catheter including a basket comprising a plurality of splines including two magnetic sensors positioned at a proximal location of the basket, in accordance with embodiments of the present disclosure. A catheter 60D can include a distal hub 64D and a proximal hub 82, a plurality of splines 66D, and a deflection control member 68D, where the proximal hub 82 further comprises a magnetic sensor 74B. The embodiment shown in FIG. 5A includes two magnetic sensors 74B (one magnetic sensor is hidden from view in FIG. 5A) in a sensor tube that is, in this embodiment, integrated with the proximal hub 82. In some embodiments (not shown), the sensor tube and the hub can be combined separate elements (e.g., see FIG. 4). In still other embodiments (not shown), the sensor tube and/or the hub can be part of a distal end of elongate shaft (e.g., a catheter).

Each of the plurality of splines 66D can have a spline distal end 84 and a spline proximal end 86. The spline distal end 84 can couple with the distal hub 64D and the spline proximal end 86 can couple with the proximal hub 82. As discussed herein, each of the spline distal ends 84 can couple with distal hub 64D through one of the plurality of distal hub spline openings 80B. As shown in FIG. 5B, each of the plurality of splines 66D can include, at the spline proximal end 86, a spline straight portion 88. The spline straight portion 88 can be aligned with a longitudinal axis, represented by the line A-A, of the proximal hub 82. In other embodiments (not shown), the proximal hub can include openings (e.g., similar to the distal hub 64C in FIG. 4) or other suitable configurations that allow the distal hub to couple with the spline proximal end.

The proximal hub 82 can include a central lumen (i.e., an opening; not visible in FIG. 5A) and some embodiments of the proximal hub 82 can include a coupler (not visible in FIG. 5A). Additional information about the central lumen and/or the coupler can be found in FIGS. 6A-C and the related discussion. The deflection control member 68D can pass through the central lumen of the proximal hub 82. Other elements (not shown in FIG. 5A) can also be located in the central lumen including, for example, control wires, electrical wires, fluid lumens, etc.).

The magnetic sensors 74B can be connected to a controller (e.g., ECU 42 of FIG. 1) and/or other electrical device by a pair of wires 78B (e.g., a twisted wire pair). The magnetic sensors 74B can allow the catheter to be tracked in a mapping system.

FIG. 5B is a side view of the distal end portion of the catheter of FIG. 5A including the two magnetic sensors positioned at the proximal location of the basket, in accordance with embodiments of the present disclosure. As described above, FIG. 5B includes two magnetic sensors 74B in a sensor tube that is integrated with the proximal hub 82.

The proximal hub 82 can be located inside a distal end of a catheter shaft or outside the distal end of a catheter shaft and coupled with the distal end of the catheter shaft (not shown). In some embodiments, the proximal hub can include integrated sensor tubes 76B for the magnetic sensors 74B (not shown).

FIGS. 6A-C show a coupler, in accordance with embodiments of the present disclosure. FIG. 6A is a cross-sectional view of a proximal end of the coupler. FIG. 6B is a side view of the coupler. FIG. 6C is a cross-sectional view of the distal end of the coupler. A coupler 90 can comprise a body 92, a proximal end 94, and a distal end 96. The distal end 96 can include a plurality of coupling locations 98 (i.e., grooves, slots, etc.) configured to couple with a proximal end of a spline (e.g., splines 66D of FIG. 5B).

In some embodiments, the proximal hub 82 can include the coupler 90. A deflection control member (e.g., deflection control member 68D) and other items (e.g., control wires, lumens, electrical wires, etc.) can pass through the central opening 99 of the coupler 90, allowing the deflection control member to be moved independently of the coupler 90. The proximal end can be coupled with a shaft or other elongate medical device (e.g., shaft 28 of FIG. 1 and/or elongated catheter body 19 of FIG. 2).

Figure 7:
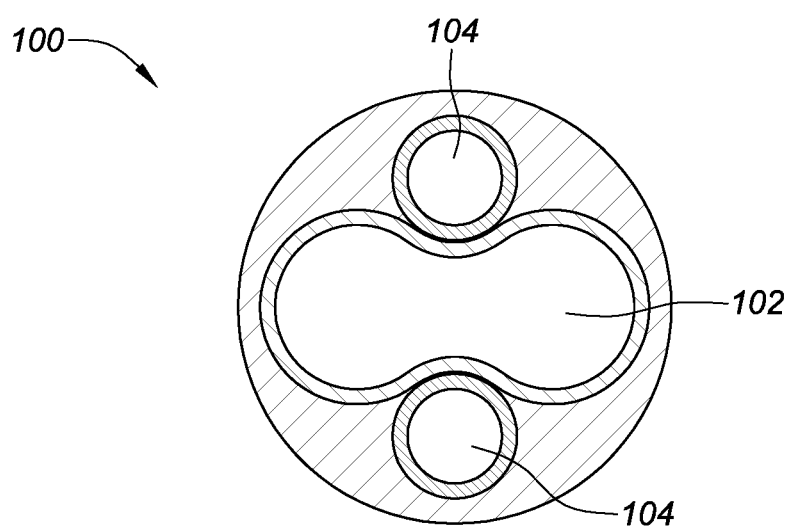
FIG. 7 is cross-sectional view of a catheter including a plurality of lumens for use with a catheter, in accordance with embodiments of the present disclosure.

FIG. 7 is a cross-sectional view of a catheter including a plurality of lumens for use with a catheter, in accordance with embodiments of the present disclosure. The catheter 100 can comprise a first lumen 102 and two second lumens 104. The first lumen can be shaped like a peanut (e.g., two circular cross-sections connected). The first lumen can contain one or more tubes (not shown) to contain (i.e. containment tubes) or house various elements such as wires for sensors, interactive elements, or similar devices and/or fluid (e.g., saline) to connect from a distal location on the catheter 100 to a proximal location.

Figure 8A:
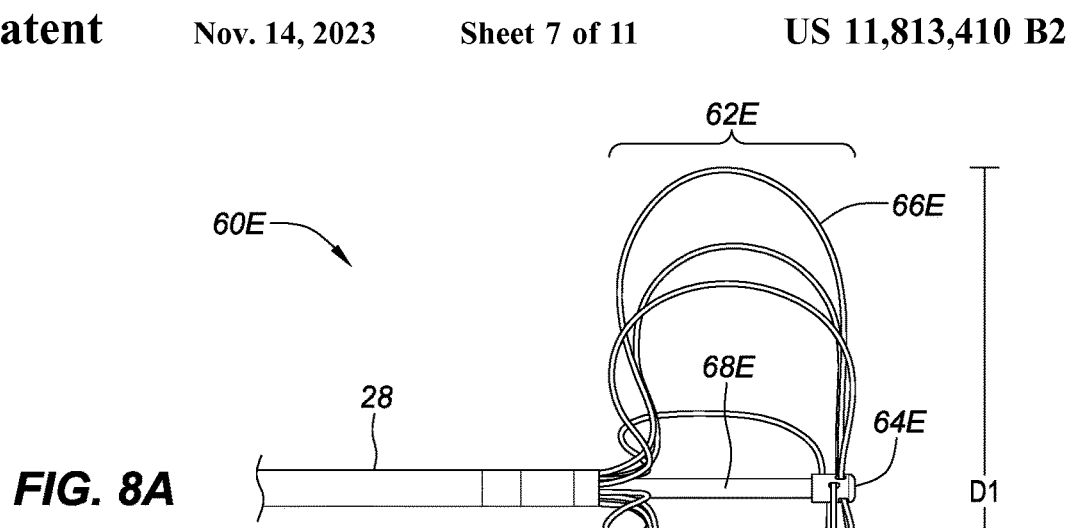
FIG. 8A is a side view of a distal end portion of a catheter including a basket comprising multiple splines and a deflection control member with the basket in a first configuration, in accordance with embodiments of the present disclosure.

FIG. 8A is a side view of a distal end portion of a catheter including a basket comprising multiple splines and a deflection control member with the basket in a first configuration, in accordance with embodiments of the present disclosure. The catheter 60E can comprise a basket 62E that is located at a distal end portion of the catheter 60E. The basket 62E can comprise a distal hub 64E and a plurality of splines 66E and a [deflection control member] 68E. Similar to other embodiments described herein, each of the plurality of splines 66E can include a plurality of interactive elements (not shown in FIG. 8A, e.g., the interactive elements 70A in FIG. 3A, where $70_x$ can represent individual interactive elements in the plurality of interactive elements $70_1$, $70_2$, $70_3$, . . . etc.).

As described herein, spacing of the plurality of interactive elements 70A can be equal or unequal. For example, in some embodiments, the plurality of interactive elements 70A can all have an equal distance between each of the plurality of interactive elements 70A (e.g., 1 mm between each electrode). In other embodiments, the spacing can vary between the plurality of interactive elements 70 (e.g., 1 mm between some of the plurality of interactive elements 70A and 2 mm between others of the plurality of interactive elements 70). In some embodiments, spacing between each of the plurality of interactive elements 70A can vary along each spline 66E and/or differ from spline to spline. Also as described herein, distribution of the plurality of interactive elements 70A can also vary between embodiments.

Figure 8B:
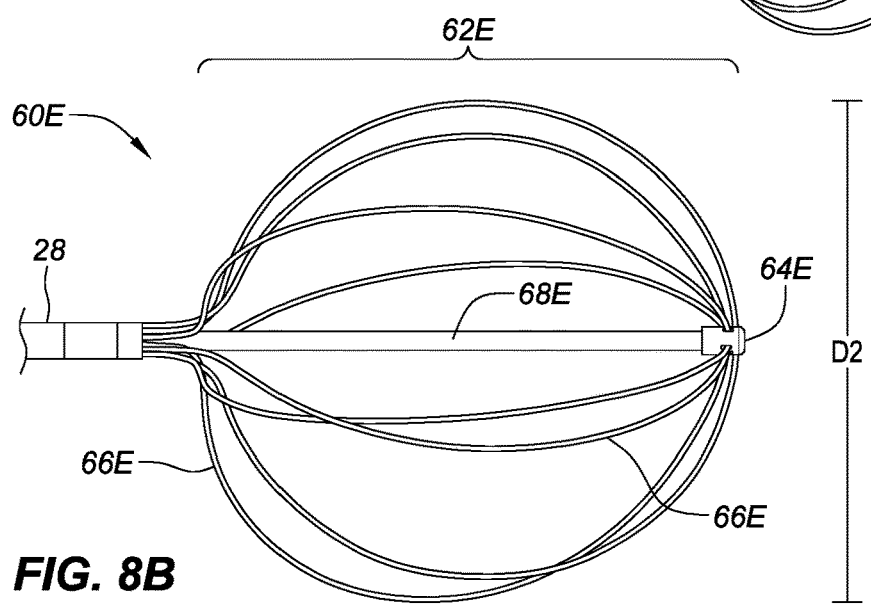
FIG. 8B is a side view of the catheter of FIG. 6A in a second configuration, in accordance with embodiments of the present disclosure.
Figure 8C:
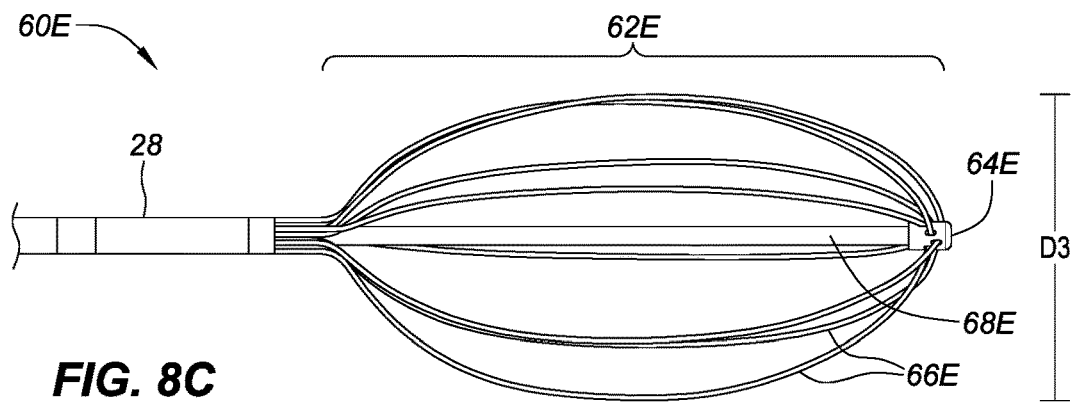
FIG. 8C is a side view of the catheter of FIG. 6A in a third configuration, in accordance with embodiments of the present disclosure.

The basket 62E can have a first deployed shape, a second deployed shape, and a third deployed shape. The basket 62E can have a diameter D1 (i.e., width) for the first deployed shape, a diameter D2 for the second deployed shape (see FIG. 8B) and a diameter D3 for the third deployed shape (see FIG. 8C) where D1 is greater than D2 and D2 is greater than D1. The basket 62E can also have an undeployed shape (i.e., undeployed configuration; not shown) that allows the basket 62E to fit inside a catheter or other elongate medical device for delivery to a location in a body. A diameter of the undeployed shape of the basket is less than D3. The second deployed shape and the third deployed shapes are shown in FIGS. 8B and 8C; see related discussion).

The deployment/undeployment of the basket 62E can be controlled by pull wires or other similar mechanisms and/or through the use of materials that are self-erecting (e.g., Nitinol). The shape of the basket 62E can vary depending on the configuration achieved using any one of the pull wires, the deflection control member 68E, and/or other deployment mechanisms.

The deflection control member 68E can have a deflection control member distal end that can be coupled with a portion of the basket 62E (e.g., the distal hub 64E) and a deflection control member proximal end (not shown in FIG. 8A) that can be coupled with a control mechanism (e.g., a portion of the handle 24 of FIG. 1 and/or handle 14A of FIG. 2). The deflection control member 68E can be a rigid element (e.g., a tube), a semi-rigid element (e.g., a flexible tube) or a flexible element (e.g., a polymer and/or metal cable, string cord or similar element).

The deflection control member 68E can move longitudinally, which can cause the basket 62E to change shape. The deflection control member 68E can be used to support a desired shape/configuration of the basket 62E. For example, the deflection control member 68E can provide support (i.e., rigidity, stiffness) to the basket 62E to maintain a specific deployed shape. In the embodiment shown in FIG. 8A, the deflection control member 68E can provide support to the basket 62E to maintain the width D1 (with respect to a longitudinal axis of the catheter 60E) of the first deployed shape. Without the support of the deflection control member 68E, the basket 62E can have a "softer" structure (i.e., reduced rigidity, more flexible) allowing the basket 62E to float with the rigidity of the basket 62E controlled by the stiffness of the splines 66E only. Adjustment of the deflection control member 68E could allow additional deflection of the basket 62E as the splines 66E and/or distal hub 64E contact tissue (e.g., the distal hub 64E could move more, allowing the spline distal ends and the spline proximal ends to have a greater range of motion, depending on the force exerted on the catheter 60E and the material properties of the splines/basket).

As the catheter 60E is deployed, the basket 62E can be pushed to contact tissue (e.g., cardiac tissue 16 in FIG. 1) and the splines 66E of the basket 62E can allow the basket to be larger than the contacted tissue (e.g., larger than a pulmonary vein). The splines 66E can also allow the basket 62E to be symmetrical or non-symmetrical depending on the configuration of the tissue contacted. The deflection control member 68E can be engaged at any time during use to change the stiffness/rigidity (i.e., stiffness profile) of the basket (and also change the shape, along with push/pull wires and other control mechanisms) as desired by the user. For example, when the deflection control member 68E is not engaged/used the basket 62E can have a first stiffness profile and the basket 62E can have a second stiffness profile when the deflection control member 68E is fully engaged and providing maximum support to the basket 62E. Additional variations in support provided by the deflection control member can allow for additional stiffness profiles of the basket (e.g., a third stiffness profile, a fourth stiffness profile, etc.).

There can be clinical scenarios where a physician could use the rigidity at the low end (e.g., when the deflection control member 68E is not being used to control the stiffness/rigidity of the basket 62E) allowing the basket 62E to be softer and less stiff/less rigid. This can allow for safer delivery/maneuverability of the basket as a smaller diameter is easier to navigate and the basket is less likely to damage tissue (e.g., during a soft apposition with tissue). Once the basket 62E is positioned at a desired location, the diameter of the basket 62E can be increased for optimal surface contact between the splines 66E and the tissue proximate the splines 66E (e.g., optimal contact between interactive elements on the splines and the tissue).

FIG. 8B is a side view of the catheter of FIG. 8A in a second configuration, in accordance with embodiments of the present disclosure. As described above, the diameter D2 of the second deployed shape of the basket 62E shown in FIG. 6B can be larger than the diameter D1 for the first deployed shape (shown in FIG. 8A), and smaller than the diameter D3 for the third deployed shape (see FIG. 8C). The second deployed shape can be achieved by using any combination of one or more of the deflection control member 68E, the structure of the splines 66E (e.g., provided by shape memory materials such as Nitinol), and push/pull wires or other control mechanisms.

With the deflection control member 68E released (e.g., loose; not being used to support and/or provide control of the shape of the basket 62E), the catheter can be pushed causing the basket 62E to contact tissue. The resistance provided by the tissue contact can allow the basket 62E to change shapes (e.g., deflect larger than the current size (e.g., see FIG. 8A). The expanded size of the basket 62E can facilitate some potential apposition opportunities with tissue, and provide an element of safety regarding damage to tissue.

With the deflection control member 68E engaged (e.g., being used to support and/or provide control of the shape of the basket 62E), the catheter can be pushed into tissue with a firmer/stiffer configuration to engage tissue as desired.

FIG. 8C is a side view of the catheter of FIG. 8A in a third configuration, in accordance with embodiments of the present disclosure. As described above, the diameter D3 of the third deployed shape of the basket 62E shown in FIG. 8C can be smaller than the diameter D1 for the first deployed shape (shown in FIG. 8A), and smaller than the diameter D2 for the second deployed shape (see FIG. 8B). The third deployed shape can be achieved by using any combination of one or more of the deflection control member 68E, the structure of the splines 66E (e.g., provided by shape memory materials such as Nitinol), and push/pull wires or other control mechanisms. With the deflection control member 72E engaged (i.e., providing support/rigidity to the basket 62E) the diameter and/or the stiffness of the basket 62E can be changed to assist in positioning relative to heart features and then the diameter and/or stiffness can be changed again to optimize contact between portions of the basket 62E and tissue.

Figure 9A:
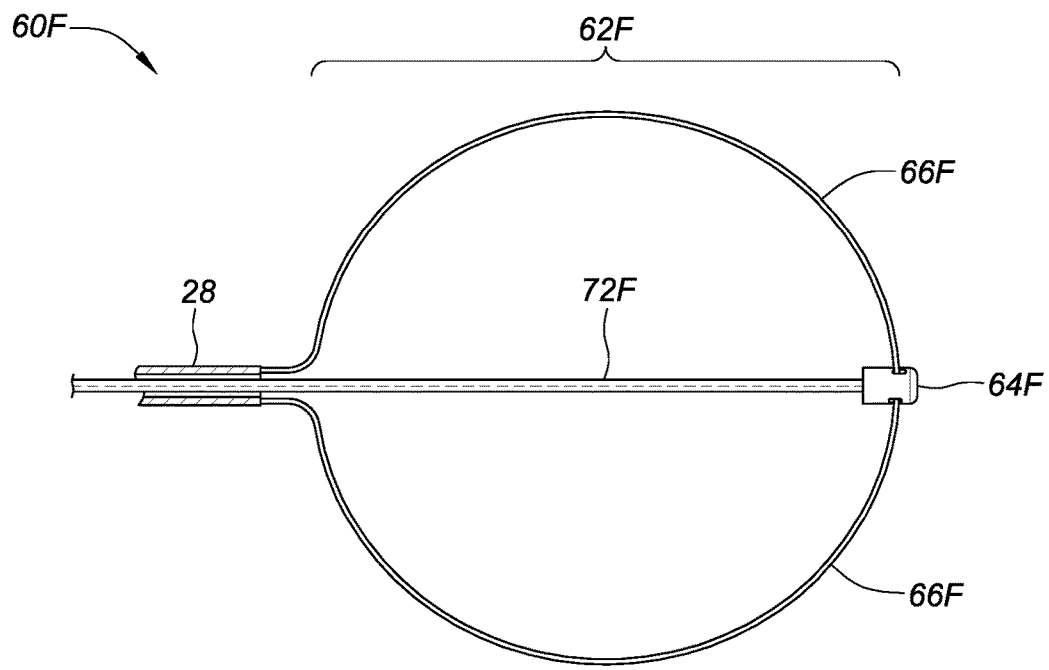
FIG. 9A is a partial cross-sectional view of a distal end portion of a catheter with a basket and a deflection control member, in accordance with embodiments of the present disclosure.

FIG. 9A is a partial cross-sectional view of a distal end portion of a catheter with a basket and a deflection control member, in accordance with embodiments of the present disclosure. A catheter 60F can include a plurality of splines 66F in a basket 62F. A distal end of the splines 66F can couple with a distal hub 64F. As shown in FIG. 9A, a distal end of a deflection control member 72F can couple with the distal hub 64F and a proximal end of the deflection control member 72F (not shown in FIG. 9A) can be located in a portion of a shaft (e.g., shaft 28 of FIG. 1 and/or elongated catheter body 19 of FIG. 2) and couple with a handle (e.g., handle 24 of FIG. 1, and/or handle 14A of FIG. 2) or some other proximal control mechanism.

The deflection control member 72F can comprise any suitable material including a polyimide (PI) tube, PI tube w/braid reinforcement, PI tube w/stainless steel wire down interior diameter of PI tube, etc. In addition, any portion (e.g., exterior surface of deflection control member 72F, interior surface proximate a wire, etc.) of the deflection control member 72F can include a coating to promote movement (reduction of friction, etc.).

The configuration of the basket 62F shown in FIG. 9A can be similar to the configuration shown in FIG. 8B and discussed above. As discussed, the deflection control member 72F can be engaged or released as desired to manipulate the amount of support/rigidity of the basket 62F.

Figure 9B:
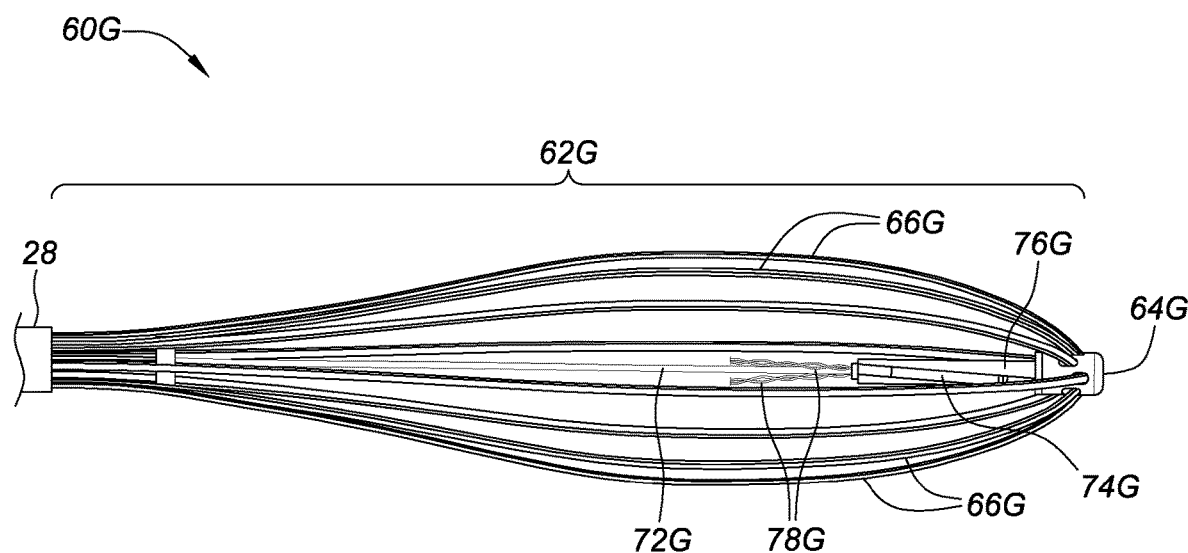
FIG. 9B is a side view of a distal end portion of a catheter similar to FIG. 3 including a basket comprising multiple splines and a deflection control member, in accordance with embodiments of the present disclosure.

FIG. 9B is a side view of a distal end portion of a catheter including a basket comprising multiple splines and a deflection control member, in accordance with embodiments of the present disclosure. A catheter 60G can include a plurality of splines 66F in a basket 62G. A distal end of the splines 66F can couple with a distal hub 64G. As shown in FIG. 9B, a distal end of a deflection control member 72G can couple with the distal hub 64G and a proximal end of the deflection control member 72F (not shown in FIG. 9B) can be located in a portion of a shaft (e.g., shaft 28 of FIG. 1 and/or elongated catheter body 19 of FIG. 2) and couple with a handle (e.g., handle 24 of FIG. 1 and/or handle 14A of FIG. 2) or some other proximal control mechanism. As described herein, the basket 62G can also include a magnetic sensor 74G coupled with the distal hub 64G. The magnetic sensor 74G can include a wire pair 78G.

As described herein, the deflection control member 72G can be used to form the third deployed shape of the basket 62G shown in FIG. 9B (similar to the configuration of basket 62E in FIG. 8B and discussed above. The shape of basket 62G can be achieved by using any combination of one or more of the deflection control member 68G, the structure of the splines 66G (e.g., provided by shape memory materials such as Nitinol), and push/pull wires or other control mechanisms. With the deflection control member 72G engaged (i.e., providing support/rigidity to the basket 62G) the diameter and/or the stiffness of the basket 62G can be changed to assist in positioning relative to heart features and then the diameter and/or stiffness can be changed again to optimize contact between portions of the basket 62G and tissue.

Figure 10A:
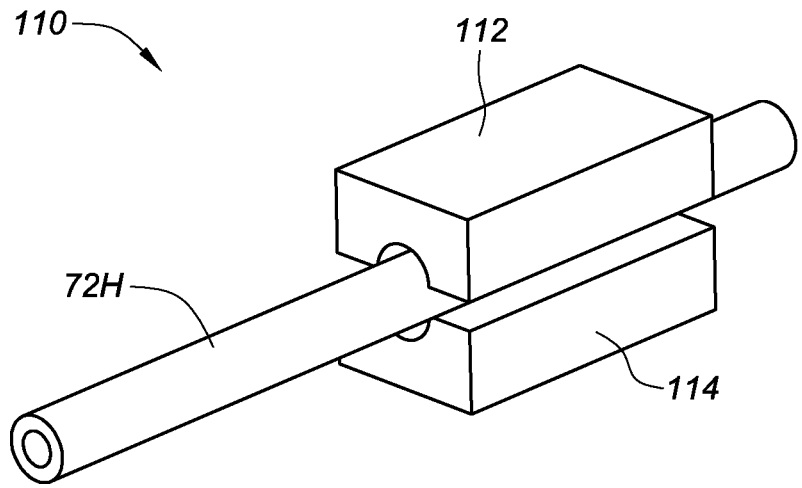
FIGS. 10A and 10B are isometric views of a clamping mechanism for limiting and/or preventing longitudinal movement of a deflection control member, where
Figure 10B:
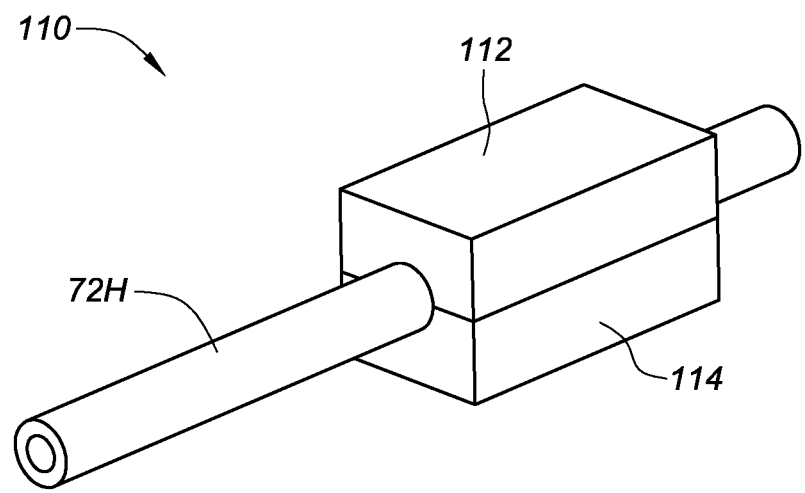

FIGS. 10A and 10B are isometric views of a movement limiter for limiting and/or preventing longitudinal movement of a deflection control member, where FIG. 10A shows the movement limiter in a first position and FIG. 10B shows the clamping mechanism (i.e., a clamp) in a second position, in accordance with embodiments of the present disclosure. A movement limiter (i.e., a clamping mechanism) 110 can comprise a first clamping element 112 and a second clamping element 114. The first clamping element 112 and the second clamping element 114 can be proximate a deflection control member 72H.

As shown in FIG. 10A, the first clamping element 112 and the second clamping element can have a first position (i.e., a neutral position, an open position, an unlocked position, etc.) where the deflection control element 72H is free to move through the clamping mechanism 110. The deflection control member 72H is either not in contact with one of the first clamping element 112 and the second clamping element 114 or both of the first clamping element 112 and the second clamping element 114. This open position can be achieved by movement of either the first clamping element 112 or the second clamping element 114 or movement of both the first clamping element 112 and the second clamping element 114 (i.e., one or more portions of the clamping element 114 is movable).

FIG. 10B shows the clamping mechanism 110 in a second position (i.e., a closed position, a locked position, etc.) where the deflection control element 72H is not free to move through the clamping mechanism 110. The clamping mechanism can use friction and/or physical deformation to prevent movement of the deflection control member 72H. Portions of the first clamping element 112 and the second clamping element 114 can be treated to increase friction between the deflection control member 72H and the first clamping element 112 and the second clamping element 114 (e.g., coatings, ridges, texture, etc.).

The closed position can include, "fully" closed and "partially" closed where fully closed prevents any longitudinal movement of the deflection control member and partially closed limits the longitudinal movement (e.g., some slippage can occur, depending on the clamping forces involved).

One embodiment of how the clamping mechanism 110 could be used is as follows:

A user could generate linear or rotational motion using a handle (e.g., handle 24 in FIG. 1) to create forward (i.e., longitudinal) motion of the deflection member (e.g., deflection member 72H). The forward motion of the deflection member would occur when the clamping mechanism is closed (i.e., clamped shut, in contact with the deflection member; see FIG. 10B) around the deflection member. If the clamping mechanism is open (e.g., FIG. 10A) the deflection member would be free to move back and forth within the open clamping mechanism.

Upon actuating a lever (e.g., moving and/or rotating a lever on the handle) the clamping mechanism could close and allow the movement of the deflection member to move and change the profile (i.e., shape) of the basket as described herein (e.g., elongate the basket with a smaller diameter as shown in FIG. 8C, or shorten the length of the basket and increase the diameter as shown in FIG. 8A). Releasing the lever would allow the basket to return to nominal size (e.g., FIG. 8B) and release the deflection member for free movement.

Figure 11A:
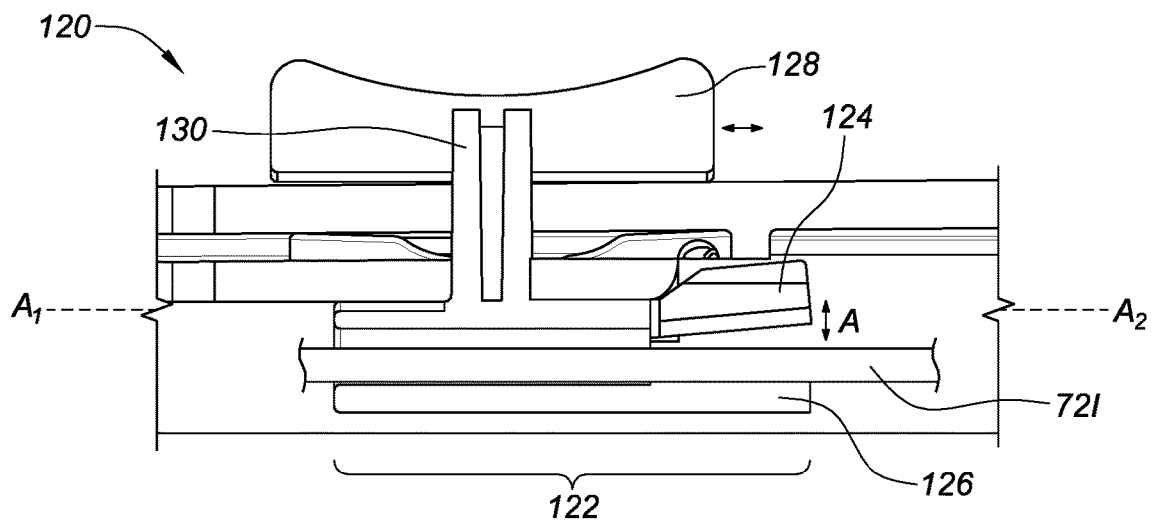
FIG. 11A is a cross-sectional view of a portion of a handle for controlling an elongated medical device including a clamping mechanism for limiting and/or preventing longitudinal movement of the elongated medical device, in accordance with embodiments of the present disclosure.

FIG. 11A is a partial cross-sectional view of a portion of a handle for controlling an elongated medical device including a selective movement limiter for preventing longitudinal movement of the elongated medical device, in accordance with embodiments of the present disclosure. A handle portion 120 can include a selective movement limiter (i.e., a clamping mechanism) 122 that includes a first clamping element 124 and a second clamping element 126, a thumb lever 128, and a thumb lever engagement post 130 coupled with the clamping mechanism 122 and the thumb lever 128.

A user can move the thumb lever 128 (e.g., slide the thumb lever 128 to the left (towards $A_1$) in a direction aligned with a longitudinal axis represented by the line $A_1$-$A_2$) that, in turn, moves the thumb lever engagement post 130 in the same direction, which can cause the clamping mechanism 122 to move (e.g., as indicated by arrow A). This movement of the clamping mechanism 122 can cause the first clamping element 124 and the second clamping element 126 to engage with the deflection control member 72I and prevent and/or limit movement of the deflection control member 72I along a longitudinal axis aligned with the line $A_1$-$A_2$.

Figure 11B:
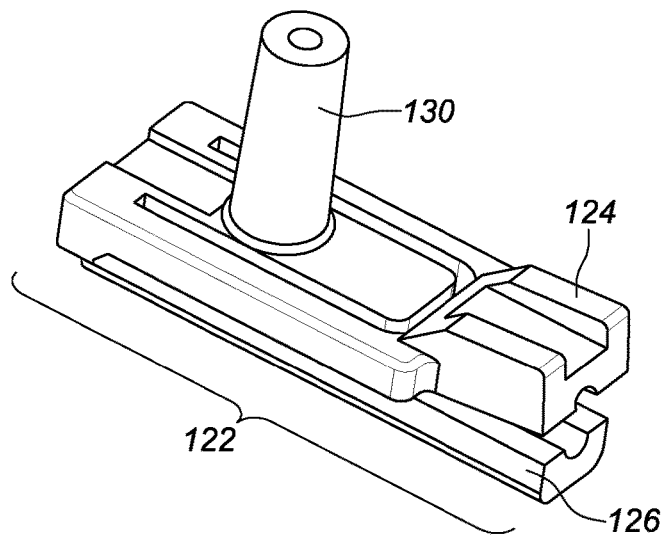
FIG. 11B is an isometric view of a portion of the clamping mechanism of FIG. 10A for preventing longitudinal movement of the elongated medical device, in accordance with embodiments of the present disclosure.

FIG. 11B is an isometric view of the clamping mechanism of FIG. 11A for limiting and/or preventing longitudinal movement of the elongated medical device, in accordance with embodiments of the present disclosure. As described above and shown in FIG. 11A, the clamping mechanism 122 can include a first clamping element 124 and a second clamping element 126. Movement of the clamping mechanism along the longitudinal axis aligned with the line $A_1$-$A_2$ can cause the first clamping element 124 and the second clamping element 126 to engage with the deflection control member 72I and prevent and/or limit movement of the deflection control member 72I. Movement of the first clamping element can occur as indicated by the arrow A shown in FIG. 11B.

As described herein, some embodiments of the clamping mechanism can include movement of both the first clamping element 124 and the second clamping element 126 (now shown in FIG. 11B; see FIG. 11B and related discussion).

Figure 11C:
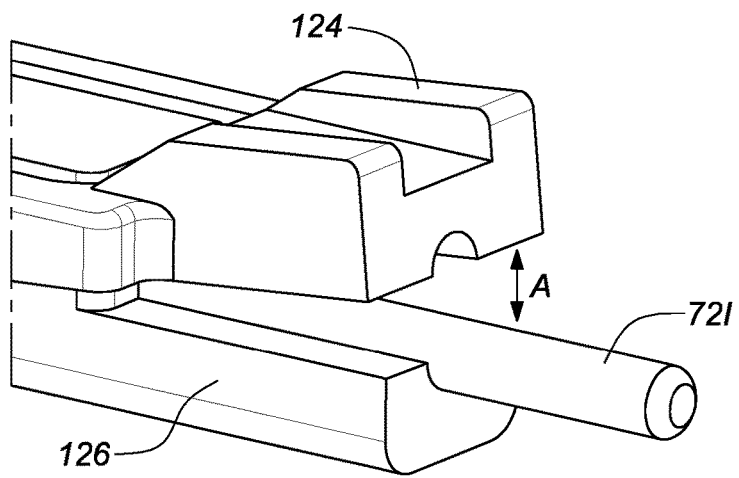
FIG. 11C is an isometric view of the mechanism of FIGS. 11A-B for preventing longitudinal movement of the elongated medical device, in accordance with embodiments of the present disclosure.

FIG. 11C is an isometric view of a portion of the clamping mechanism of FIGS. 11A-B for preventing longitudinal movement of the elongated medical device, in accordance with embodiments of the present disclosure.

FIG. 12A is a side view of a portion of the a catheter including a basket comprising multiple splines with a first spline shape, in accordance with embodiments of the present disclosure. A catheter 60J can comprise a distal hub 64J and a plurality of splines 66J (two splines 66J are shown; additional splines omitted from this view) as shown in FIG. 12A. Each of the plurality of splines 66J can have a first spline shape as shown in FIG. 12A, where the spline comprises one or more curved portions. The curved portions can each have a radius that is the same (e.g., the side view of the two splines 66J essentially form a circle) as shown in FIG. 12A.

The shape of the splines shown in FIG. 12A allows the distal hub 64J to be the first portion of the catheter 60J to contact tissue 140A (e.g., endocardium tissue) as the catheter 60J is moved distally. The curvature of the curved portions of the plurality of splines 66J can allow interactive elements (not shown in FIG. 12A; described herein such as interactive elements 70A, 70B in FIGS. 3A-B) on the splines 66J to have an area of interactive element coverage 142 (e.g., 142A, 142B, 142C). The area of interactive element coverage 142 can be larger or smaller than the area shown in FIG. 12A depending on the number and/or placement of interactive elements on the splines.

As seen in FIG. 12A, the curvature of the plurality of splines 66J. combined with the number and/or placement of interactive elements, does not allow much, if any, contact between the endocardium tissue 140A and a distal portion of the area of electrode coverage 142A. Contact between the endocardium tissue 140A and the interactive elements can be increased by, for example, changing the shape of the splines (e.g., adjusting a size of the basket of the catheter using push/pull wires and/or a deflection control member-see FIGS. 8A-C and related discussion as an example) or by increasing force in the distal direction. Additional distal force on the catheter may cause the tissue to deform and increase contact with the area of electrode coverage 142A. However, the excessive additional distal force can also cause tissue damage due to the distal hub 64J.

Similarly, the curvature of the plurality of splines 66J shown in FIG. 12A (e.g., one radius for the entire spline), combined with the number and/or placement of interactive elements, does not allow much, if any, contact with the endocardium tissue 140A and a proximal portion of the area of electrode coverage 142C. As discussed above, changing the shape of the splines and/or using additional force (in this case, additional proximal force) could increase contact between proximal interactive elements (not shown in FIG. 12A, see, e.g., electrode $70_{prox}$ in FIG. 3B). and endocardium tissue 140B.

FIG. 13B is a side view of a portion of a catheter including a basket comprising multiple splines with a second spline shape for increased contact between proximal portions of the spline and tissue, in accordance with embodiments of the present disclosure. A catheter 60K can comprise a distal hub 64K and a plurality of splines 66K (two splines 66K are shown; additional splines omitted from this view) as shown in FIG. 12B. Each of the plurality of splines 66K can have a first spline shape as shown in FIG. 12B, where the spline comprises one or more curved portions. The curved portions can have an different radii (e.g., the side view of the two splines 66K essentially form a circle), especially at a distal portion of the splines (e.g., proximate the hub 64K) and a proximal portion of the splines. The multiple radii for the curve portions can allow a portion of the spline, and therefore a portion of the interactive elements on the spline, to contact tissue first. The greater the amount of the distal spline portion and/or the proximal spline portion that is parallel to the tissue (i.e., flatter), the greater the amount of interactive elements that can contact the tissue. For example, when moved distally, interactive elements on the catheter 60K can contact tissue 140B (e.g., endocardium tissue) at an area of electrode coverage 142C at a proximal portion of the splines can contact the tissue 140B.

As described herein, changing the shape of the catheter (e.g., adjusting a size of the basket of the catheter using push/pull wires and/or a deflection control member-see FIGS. 8A-C and related discussion as an example) can allow contact between a higher number of interactive elements and tissue 140B.

Although at least one embodiment of an apparatus for detecting catheters to introducers has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements and can also include elements that are part of a mixture or similar configuration. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An elongate medical device, comprising:
    an expandable structure with an expandable configuration and a collapsed configuration;
    a handle, operably coupled to the expandable structure, the handle further including a selective movement limiter that is housed inside of the handle; and
    a deflection control member coupled with a distal hub, where the deflection control member is configured to adjust a stiffness of the expandable structure, from a first stiffness to a second stiffness, and maintain the first stiffness or the second stiffness when the selective movement limiter couples with the deflection control member and limits a longitudinal movement of the deflection control member;
    wherein the deflection control member is configured to move freely when the selective movement limiter is not coupled with the deflection control member.

2. The elongate medical device of claim 1, wherein the expandable structure comprises a plurality of splines, wherein each of the plurality of splines includes a spline proximal end and a spline distal end.

3. The elongate medical device of claim 2, further comprising a proximal hub, where each of the spline proximal ends is coupled with the proximal hub.

4. The elongate medical device of claim 2, wherein a spline distal end portion of one or more of the plurality of splines comprises a first spline shape and a second spline shape.

5. The elongate medical device of claim 1, wherein the deflection control member comprises a semi-rigid material.

6. The elongate medical device of claim 5, wherein the semi-rigid material comprises a polymer.

7. The elongate medical device of claim 1, further comprising a magnetic sensor.

8. The elongate medical device of claim 7, wherein the magnetic sensor is coupled with the distal hub.

9. The elongate medical device of claim 7, wherein the magnetic sensor is coupled with a proximal hub.

10. The elongate medical device of claim 1, wherein each of the expandable structure further comprises a plurality of interactive elements.

11. The elongate medical device of claim 10, wherein the expandable structure comprises a plurality of splines and the plurality of interactive elements are equally distributed on each of the plurality of splines.

12. The elongate medical device of claim 10, wherein the plurality of interactive elements are unequally spaced on each of the plurality of interactive elements.

13. The elongate medical device of claim 10, wherein one or more the plurality of interactive elements are positioned proximate a spline proximal end.

14. The elongate medical device of claim 10, wherein the plurality of interactive elements further comprise one or more of an electrode, an energy delivery element, a thermocouple, a force sensor, a strain gauge, a strain sensor, a position sensor, a biosensor, a diagnostic sensor, a therapy sensor, a chemical sensor, a light-emitting sensor, an acoustic sensor, an ultrasound sensor, an energy receiving and/or measuring sensor, a magnetic coil or sensor, and a thermoelectric element.

15. The elongate medical device of claim 10, wherein the plurality of interactive elements further comprises an electrode.

16. The elongate medical device of 1, wherein the selective movement limiter comprises a first portion and a second portion, where the first portion is in a fixed position and the second portion is movable to engage with the deflection control member by clamping the deflection control member with the first portion in order to limit the longitudinal movement of the deflection control member.

17. The elongate medical device of 1, wherein the selective movement limiter comprises a first portion and a second portion, where the first portion and the second portion are movable to engage with the deflection control member by clamping the deflection control member in order to limit the longitudinal movement of the deflection control member.

18. An elongate medical device comprising:
an expandable structure comprising:
- a plurality of splines where each has a spline proximal end and a spline distal end; and
- a distal hub, where each of the spline distal ends is coupled with the distal hub;

a deflection control member coupled with the distal hub, where the deflection control member is configured to:
- adjust a stiffness of the expandable structure, from a first stiffness to a second stiffness; and
- maintain the first stiffness or the second stiffness; and a handle, wherein the handle includes a clamp, wherein the clamp is housed inside of the handle and engages the deflection control member and limits a longitudinal movement of the deflection control member.

19. The elongate medical device of claim 18, wherein the deflection control member is a means for adjusting the stiffness of the expandable structure from the first stiffness to the second stiffness.

20. The elongate medical device of 18, wherein the clamp comprises a first portion and a second portion, where the first portion is in a fixed position and the second portion is movable relative to the first portion to allow engagement with the deflection control member.

21. The elongate medical device of 18, wherein the clamp comprises a first portion and a second portion, where the first portion and the second portion are movable to allow engagement with the deflection control member.

22. An elongate medical device, comprising:
- a handle comprising a control mechanism and a selective movement limiter, wherein the selective movement limiter is housed inside of the handle;
- a catheter shaft having a catheter shaft proximal end and a catheter shaft distal end, wherein the catheter shaft proximal end is coupled to the handle;
- an expandable structure comprising elongated splines and a distal hub, wherein the expandable structure has an undeployed shape and a deployed shape, wherein the expandable structure is radially outward expandable from the undeployed shape to the deployed shape and inwardly collapsible from the deployed shape to the undeployed shape, wherein each of the elongated splines is coupled to and extends between the catheter shaft distal end and the distal hub;
- a deflection control member having a distal end coupled to the distal hub, wherein the control mechanism is drivingly coupled with the distal hub via the deflection control member and operable to move the deflection control member distally relative to the catheter shaft to inwardly collapse the expandable structure from the deployed shape to the undeployed shape and move the deflection control member proximally relative to the catheter shaft to radially outwardly expand the expandable structure from the undeployed shape to the deployed shape, and wherein the selective movement limiter is operable to limit movement of the deflection control member relative to the catheter shaft.

* * * * *